US010912764B2

(12) United States Patent
Fenical et al.

(10) Patent No.: US 10,912,764 B2
(45) Date of Patent: *Feb. 9, 2021

(54) SALINOSPORAMIDES AND METHODS OF USE THEREOF

(71) Applicant: The Regents of the University of California, Oakland, CA (US)

(72) Inventors: William Fenical, Del Mar, CA (US); Paul Jensen, San Diego, CA (US); Tracy Mincer, San Diego, CA (US); Robert H. R. Feling, Wiesbaden (DE)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/418,801

(22) Filed: May 21, 2019

(65) Prior Publication Data

US 2019/0269651 A1 Sep. 5, 2019

Related U.S. Application Data

(60) Continuation of application No. 15/655,739, filed on Jul. 20, 2017, now Pat. No. 10,314,818, which is a continuation of application No. 14/794,468, filed on Jul. 8, 2015, now Pat. No. 9,713,607, which is a continuation of application No. 14/139,692, filed on Dec. 23, 2013, now Pat. No. 9,078,881, which is a division of application No. 13/477,364, filed on May 22, 2012, now Pat. No. 8,637,565, which is a continuation of application No. 12/638,860, filed on Dec. 15, 2009, now Pat. No. 8,222,289, which is a continuation of application No. 11/705,694, filed on Feb. 12, 2007, now Pat. No. 7,635,712, which is a continuation of application No. 11/147,622, filed on Jun. 7, 2005, now Pat. No. 7,176,233, which is a division of application No. 10/838,157, filed on Apr. 30, 2004, now Pat. No. 7,176,232, which is a continuation-in-part of application No. 10/600,854, filed on Apr. 30, 2003, now Pat. No. 7,179,834.

(60) Provisional application No. 60/391,314, filed on Jun. 24, 2002.

(51) Int. Cl.
| | |
|---|---|
| *A61K 31/407* | (2006.01) |
| *A61K 31/397* | (2006.01) |
| *A61K 31/424* | (2006.01) |
| *A61K 31/43* | (2006.01) |
| *C07D 491/04* | (2006.01) |
| *C12P 17/18* | (2006.01) |
| *A61K 45/06* | (2006.01) |
| *C07D 491/044* | (2006.01) |

(52) U.S. Cl.
CPC .......... *A61K 31/407* (2013.01); *A61K 31/397* (2013.01); *A61K 31/424* (2013.01); *A61K 31/43* (2013.01); *A61K 45/06* (2013.01); *C07D 491/04* (2013.01); *C07D 491/044* (2013.01); *C12P 17/18* (2013.01); *C12P 17/188* (2013.01)

(58) Field of Classification Search
None
See application file for complete search history.

(56) References Cited

U.S. PATENT DOCUMENTS

| | | |
|---|---|---|
| 5,445,829 A | 8/1995 | Paradissis et al. |
| 5,576,012 A | 11/1996 | Bauer et al. |
| 5,601,845 A | 2/1997 | Buxton et al. |
| 5,641,515 A | 6/1997 | Ramtoola |
| 5,653,987 A | 8/1997 | Modi et al. |
| 5,654,286 A | 8/1997 | Hostetler |
| 5,667,809 A | 9/1997 | Trevino et al. |
| 5,683,676 A | 11/1997 | Akehurst et al. |
| 5,688,529 A | 11/1997 | Lidgate et al. |
| 5,707,615 A | 1/1998 | Cardin et al. |
| 5,707,641 A | 1/1998 | Gertner et al. |
| 5,726,181 A | 3/1998 | Hausheer et al. |
| 5,733,888 A | 3/1998 | Carver et al. |
| 5,756,764 A | 5/1998 | Fenteany et al. |
| 5,874,443 A | 2/1999 | Kiely et al. |
| 5,886,210 A | 3/1999 | Rayle et al. |
| 5,922,683 A | 7/1999 | Or et al. |
| 6,133,308 A | 10/2000 | Soucy et al. |
| 6,147,223 A | 11/2000 | Fenteany et al. |

(Continued)

FOREIGN PATENT DOCUMENTS

| | | |
|---|---|---|
| CA | 2429163 | 6/2002 |
| EP | 04 77 6728 | 6/2008 |

(Continued)

OTHER PUBLICATIONS

Adams et al "Proteasome Inhibitors: A Novel Class of Potent and Effective Antitumor Agents", *Cancer Res.*, (1999) 59:2615-2622 (1999).

Adams, J., "Proteasome Inhibitors as New Anticancer Drugs", *Curr. Opin. Oncol.*, 14:628-34 (2002).

Adams, J., "The Development of Novel Targeted Therapeutics for Treatment of Multiple Myeloma Research Roundtable", *Eur. J. Haematol*, 70:265 (2003).

Alessandri et al., "Mobilization of Capillary Endothelium In Vitro Induced by Effectors of Angiogenesis In Vivo", *Cancer Res.*, 43(4):1790-1797 (1983).

(Continued)

*Primary Examiner* — Samantha L Shterengarts
(74) *Attorney, Agent, or Firm* — DLA Piper LLP (US)

(57) ABSTRACT

The present invention is based on the discovery that certain fermentation products of the marine actinomycete strains CNB392 and CNB476 are effective inhibitors of hyperproliferative mammalian cells. The CNB392 and CNB476 strains lie within the family Micromonosporaceae, and the generic epithet Salinospora has been proposed for this obligate marine group. The reaction products produced by this strain are classified as salinosporamides, and are particularly advantageous in treating neoplastic disorders due to their low molecular weight, low $IC_{50}$ values, high pharmaceutical potency, and selectivity for cancer cells over fungi.

12 Claims, 17 Drawing Sheets

(56) References Cited

U.S. PATENT DOCUMENTS

| | | |
|---|---|---|
| 6,214,862 B1 | 4/2001 | Fenteany et al. |
| 6,271,199 B2 | 8/2001 | Brand et al. |
| 6,294,560 B1 | 9/2001 | Soucy et al. |
| 6,333,358 B1 | 12/2001 | Nakazato et al. |
| 6,335,358 B1 | 1/2002 | Fenteany et al. |
| 6,350,759 B1 | 2/2002 | Cesare et al. |
| 6,458,825 B1 | 10/2002 | Fenteany et al. |
| 6,500,825 B1 | 12/2002 | Lan et al. |
| 6,506,787 B2 | 1/2003 | Fujisnita et al. |
| 6,509,331 B1 | 1/2003 | Audia et al. |
| 6,566,553 B2 | 5/2003 | Soucy et al. |
| 6,645,999 B1 | 11/2003 | Schreiber et al. |
| 6,794,516 B2 | 9/2004 | Soucy et al. |
| 6,838,477 B2 | 1/2005 | Schreiber et al. |
| 6,849,743 B2 | 2/2005 | Soucy et al. |
| 7,144,723 B2 | 12/2006 | Fenical et al. |
| 7,176,233 B2 | 2/2007 | Fenical et al. |
| 7,179,834 B2 | 2/2007 | Fenical et al. |
| 7,183,417 B2 | 2/2007 | Corey |
| 7,276,530 B2 | 10/2007 | Potts et al. |
| 7,371,875 B2 | 5/2008 | Xiao et al. |
| 7,442,830 B1 | 10/2008 | Olhava et al. |
| 7,511,156 B2 | 3/2009 | Corey |
| 7,544,814 B2 | 6/2009 | Potts et al. |
| 7,572,606 B1 | 8/2009 | Lam et al. |
| 7,579,371 B2 | 8/2009 | Palladino et al. |
| 7,635,712 B2 | 12/2009 | Fenical |
| 7,879,576 B2 | 2/2011 | Fenical et al. |
| 7,910,616 B2 | 3/2011 | Macherla et al. |
| 7,928,138 B2 | 4/2011 | Feling et al. |
| 8,217,072 B2 | 7/2012 | Fenical et al. |
| 8,222,289 B2 | 7/2012 | Fenical |
| 8,637,565 B2 | 1/2014 | Fenical |
| 9,078,881 B2 | 7/2015 | Fenical |
| 2001/0002391 A1 | 5/2001 | Brand et al. |
| 2001/0051654 A1 | 12/2001 | Elliott et al. |
| 2002/0049157 A1 | 4/2002 | Wu et al. |
| 2002/0068690 A1 | 6/2002 | Baldwin et al. |
| 2002/0106689 A1 | 8/2002 | Faustman et al. |
| 2003/0157695 A1 | 8/2003 | Fenical et al. |
| 2004/0106539 A1 | 6/2004 | Schubert et al. |
| 2004/0138196 A1 | 7/2004 | Fenical et al. |
| 2005/0049294 A1 | 3/2005 | Palladino et al. |
| 2005/0203029 A1 | 9/2005 | Schubert et al. |
| 2005/0203162 A1 | 9/2005 | Xiao et al. |
| 2005/0228186 A1 | 10/2005 | Corey |
| 2005/0239866 A1 | 10/2005 | Fenical et al. |
| 2005/0245435 A1 | 11/2005 | Smyth et al. |
| 2005/0288352 A1 | 12/2005 | Potts et al. |
| 2006/0008852 A1 | 1/2006 | Fenical et al. |
| 2006/0229353 A1 | 10/2006 | Stadler et al. |
| 2006/0264495 A1 | 11/2006 | Palladino et al. |
| 2006/0287520 A1 | 12/2006 | Danishefsky et al. |
| 2007/0004676 A1 | 1/2007 | Palladino |
| 2007/0155815 A1 | 7/2007 | Fenical et al. |
| 2007/0161693 A1 | 7/2007 | Corey |
| 2007/0225350 A1 | 9/2007 | Anderson et al. |
| 2007/0249693 A1 | 10/2007 | Ling et al. |
| 2008/0070273 A1 | 3/2008 | Fenical et al. |
| 2008/0070969 A1 | 3/2008 | Potts et al. |
| 2008/0280968 A1 | 11/2008 | Palladino et al. |
| 2009/0022730 A1 | 1/2009 | Raulf et al. |
| 2009/0036390 A1 | 2/2009 | Anderson et al. |
| 2009/0062547 A1 | 3/2009 | Romo et al. |
| 2009/0069401 A1 | 3/2009 | Fenical et al. |
| 2009/0148445 A1 | 6/2009 | Bonavida et al. |
| 2009/0156469 A1 | 6/2009 | Ghobrial et al. |
| 2009/0197937 A1 | 8/2009 | Fenical et al. |
| 2009/0234137 A1 | 9/2009 | Ling et al. |
| 2009/0298906 A1 | 12/2009 | Macherla et al. |
| 2009/0318529 A1 | 12/2009 | Fenical et al. |
| 2010/0144826 A1 | 6/2010 | Fenical et al. |
| 2010/0168046 A1 | 7/2010 | Palladino et al. |

FOREIGN PATENT DOCUMENTS

| | | |
|---|---|---|
| WO | WO 1996/032105 A1 | 10/1996 |
| WO | WO 1998/035691 A1 | 8/1998 |
| WO | WO 1999/009006 A1 | 2/1999 |
| WO | WO 1999/015183 A1 | 4/1999 |
| WO | WO 1999/022729 A1 | 5/1999 |
| WO | WO 2000/023614 A1 | 4/2000 |
| WO | WO 2002/047610 A2 | 6/2002 |
| WO | WO 2004/043374 A2 | 5/2004 |
| WO | WO 2004/071382 A2 | 8/2004 |
| WO | WO 2005/002572 A2 | 1/2005 |
| WO | WO 2005/003137 A1 | 1/2005 |
| WO | WO 2005/094423 A2 | 10/2005 |
| WO | WO 2005/099687 A2 | 10/2005 |
| WO | WO 2006/005551 A1 | 1/2006 |
| WO | WO 2006/028525 A2 | 3/2006 |
| WO | WO 2006/060609 A1 | 6/2006 |
| WO | WO 2006/060676 A1 | 6/2006 |
| WO | WO 2006/060809 A2 | 6/2006 |
| WO | WO 2006/060819 A2 | 6/2006 |
| WO | WO 2006/118973 A2 | 11/2006 |
| WO | WO 2007/021897 A1 | 2/2007 |
| WO | WO 2007/033039 A2 | 3/2007 |
| WO | WO 2007/130404 A1 | 11/2007 |
| WO | WO 2007/138116 A2 | 12/2007 |
| WO | WO 2008/124699 A1 | 10/2008 |
| WO | WO 2008/137780 A2 | 11/2008 |
| WO | WO 2009/134531 A2 | 11/2009 |
| WO | WO 2009/140287 A1 | 11/2009 |

OTHER PUBLICATIONS

Alm et al., "Effects of Topically Applied PGF2 and its Isopropylester on Normal and Glaucomatous Human Eyes", *Prog. Clin. Biol. Res.*, (1989) 312:447-58.

Andtbacka et al., "The Proteasome Inhibitor NPI-0052 Overcomes TRAIL Resistance in Human Pancreatic Cancer Cells In Vitro and In Vivo", *Cancer Research*, (2007) (under revision).

Barral et al., "The Proteasome Inhibitor NPI-0052 Reduces Tumor Growth and Overcomes Resistance of Prostate Cancer to rhTRAIL via Inhibition of the NE-kB Pathway", *Amer. Assoc. Cancer Res.*, (2007): abstract 1465.

Beers et al. (Eds), "The Merck Manual of Diagnosis and Therapy", 17th Ed. 1999, The Merck Research Laboratories, Whitehouse Station N.J., pp. 1085-1088, 1101-1135, and 1237-1276.

Beers et al. (Eds.), "Bacterial Diseases," *The Merck Manual of Diagnosis and Therapy*, (1999) The Merck Research Laboratories, Whitehouse Station N.J., Section 13, Chapter 157:1157-1158.

Beers et al. (Eds.), "Parasitic Infections," *The Merck Manual of Diagnosis and Therapy*, (1999) The Merck Research Laboratories, Whitehouse Station N.J., Section 13, Chapter 161:1241-1252.

Beers et al. (Eds.), *The Merck Manual of Diagnosis and Therapy*, 17th Ed. 1999, The Merck Research Laboratories, Whitehouse Station N.J., pp. 397-399, 948-949, 1916-1917, 1974-1975 and 1978-1983.

Bernan et al., "Marine Microorganisms as a Source of New Natural Products", Advances in Applied Microbiology (1997), 43:57-90, Academic Press, Inc.

Bhalla et al., "High-Dose Mitoxantrone Induces Programmed Cell Death or Apoptosis in Human Myeloid Leukemia Cells", Blood, 82(10):3133-3140 (1993).

Bicknell et al. (Eds.), Tumour Angiogenesis, Oxford University Press, New York (1997), Table of Contents, pp. 5.

Blum et al., "Adriamycin: A New Anticancer Drug with Significant Clinical Activity", Ann. Intern. Med., 80(2):249-259 (1974).

Blunt et al., "Marine Natural Products", Nat. Prod. Rep., 20:1-48, The Royal Society of Chemistry (2003).

Bodart et al., "Anthrax, MEK and Cancer", Cell Cycle, 1:10-15 (2002).

Bradley et al., "Identification of the Cellular Receptor for Anthrax Toxin", Nature, 414:225-229 (2001).

Brosius et al., "Complete Nucleotide Sequence of a 16S Ribosomal RNA Gene from *Eschericia coli*", Biochemistry, 75(10):4801-4805 (1978).

(56) References Cited

OTHER PUBLICATIONS

Brosius et al., "Complete Nucleotide Sequence of a 16S Ribosomal RNA Gene from *Eschericia coli*", Biochemistry, 75(10):4801-5 (1978).
Bull et al., "Search and Discovery Strategies for Biotechnology: the Paradigm Shift", Microbiology and Molecular Biology Reviews (2000), 64(3):573-606, American Society for Microbiology.
Carey, Francis, Organic Chemistry, 2nd ed., McGraw Hill, Inc., New York (1992), pp. 328-331.
Chatterjee et al., "RKIP Sensitizes Prostate and Breast Cancer Cells to Drug-induced Apoptosis", The Journal of Biological Chemistry, 279(17):17515-17523 (2004).
Chauhan et al. "A Novel Orally Available Proteasome Inhibitor NPI-0052 Induces Killing in Multiple Myeloma (MM) Cells Resistant to Conventional and Bortezomib Therapies", Blood, 104(11):2405 (2004).
Chauhan et al., "A Novel Orally Active Proteasome Inhibitor Induces Apoptosis in Multiple Myeloma Cells with Mechanisms Distinct from Bortezomib", Cancer Cell, 8:407-419 (2005).
Chauhan et al., "A Novel Proteasome Inhibitor NPI-0052 as an Anticancer Therapy", British Journal of Cancer, 95(8):961-965 (2006).
Cheng et al., "Arenaric Acid, a New Pentacyclic Polyether Produces by a Marine Bacterium (Actinomycetales)", J. Nat. Prod. (1999), 62:605-607, American Chemical Society and American Society of Pharmacognosy.
Cheng et al., "Luisols A and B, New Aromatic Tetraols Produced by an Estuarine Marine Bacterium of the genus *Streptomyces* (Actinomycetales)", J. Nat. Prod. (1999) 62:608-610, American Chemical Society and American Society of Pharmacognosy.
Chow et al., "Anti-CD20 antibody (IDEC-C2B8, rituximab) Enhances Efficacy of Cytotoxic Drugs on 5 Neoplastic Lymphocytes in vitro: Role of Cytokines, Complement, and Caspases", Haematologica, 87:33-43 (2002).
Ciechanover et al., (Eds.) "The Ubiquitin-Proteasome Proteolytic System—From Classical Biochemistry to Human Diseases" by Baumeister et al., pp. 68-70 (2002).
Claverol et al., "Mapping and Structural Dissection of Human 20 S Proteasome Using Proteomic Approaches", Mol. Cell. Proteomics, (2002) 1:567-78.
Cole et al. "The Ribosomal Database Project (RDP-11): Sequences and Tools for High-Throughput rRna Analysis," Nucleic Acids Research, 33:D294-D296 (2005).
Colquhoun et al, "Rapid Characterization of Deep-Sea Actionmycetes for Biotechnology Screening Programmes", Antonie Van Leeuwenoek, 77:359-367 (2000).
Colquhoun et al., "Novel Rhodococci and Other Mycolate Actinomycetes from the Deep Sea", Antonie van Leeuwenhoek (1998), 74:27-40, Khwer Academic Publishers.
Colquhoun et al., "Taxonomy and Biotransformation Activities of Some Deep-See Actinomycetes", Extremophiles, 2:269-277, Springer-Verlag (1998).
Corey et al., "An Efficient Total Synthesis of a New and Highly Active Analog of Lactacystin", Tetrahedron Letters, 39:7475-7478 (1998).
Corey et al., "The Structural Requirements for Inhibition of Proteasome Function by the Lactacystinderived beta-lactone and Synthetic Analogs", Tetrahedron, 55(11):3305-3316 (1999).
Corey et al., "Total Synthesis of Lactacystin", J. Am. Chem. Soc., 114(26):10677-10678 (1992).
Cragg et al., "Chemical Diversity: A Function of Biodiversity", Trends Pharmacol. ScL, 23:404-5 (2002).
Crane et al., "A novel enantioselective synthetic route to omuralide analogues with the potential for species selectivity in proteasome inhibition", Organic Letters, 1395-1397 (2001).
Crueger et al. (Eds.), Biotechnology: A Textbook of Industrial Microbiology, 2nd ed. (English Edition, Thomas D. Brock Ed.), Sinauer Associates Inc., Sunderland MA, (1990) Chapter 2:4-8.
Cusack et al., "Enhanced Chemosensitivity to CPT-11 with Proteasome Inhibitor PS-341:Implications for Systemic Nuclear Factor-kB Inhibition", Cancer Res., 61 (9):3535-40 (2001).
Cusack et al., "NPI-0052 Enhances Tumoricidal Response to Conventional Cancer Therapy in a Colon Cancer Model", Clin. Cancer Res., 22:6758-6764 (2006).
Cusack et al., "Oral proteasome inhibitor (NP1-0052) enhances sensitivity to combination Gemcitabine and Erbitux in a pancreatic cancer xenograft model", Nereus Pharmaceuticals, Inc., (Apr. 19, 2005), abstract 4943 for presentation at the American Association of Cancer Research Annual Meeting held on Apr. 19, 2005 in Orange County, CA, 1 page.
Cusack et al., "Rationale for the Treatment of Solid Tumors with the Proteasome Inhibitor Bortezomib", Cancer Treat Rev., 29(Suppl1):21-31 (2003).
Davidson B. S., "New Dimensions in Natural Products Research: Cultured Marine Microorganisms", Current Opinion in Biotechnology, 6:284-291 (1995), Current Biology Ltd.
Decker et al., "Inhibition of Caspase-3-mediated Poly (ADP-ribose) Polymerase (PARP) Apoptotic Cleavage by Human PARP Autoantibodies and Effect on Cells Undergoing Apoptosis," J. Biol. Chem., 275(12):9043-9046 (2000).
Delong et al., "Environmental Diversity of Bacteria and Archaea", Syst. Biol., 50(4):470-478 (2001).
Developmental Therapeutics Program—NCI/NIH, "Cell Lines in the in Vitro Screen", online:http://dtp._nci._nih.gov/docs/misc/common_files/cell_listlhtml, accessed Oct. 27, 2009.
Developmental Therapeutics Program—NCI/NIH, "DTP Human Tumor Cell Line Screen". Screening Services. DPI. Sep. 28, 2005 http://dtp.nci.nih.gov/branches/btb/ivclsp.html.
Dick et al., "Mechanistic Studies on the Inactivation of the Proteasome by Lactacystin", J. Biol. Chem., 271 (13):7273-7276 (1996).
Ding et al., "Proteasome Inhibition Induces Reversible Impairments in Protein Synthesis", The FASEB Journal, 20:1055-1063 (2006).
Duesbery et al., "Proteolytic Inactivation of MAP-Kinase-Kinase by Anthrax Lethal Factor", Science, 280:734-737 (1998).
EFS File History of U.S. Appl. No. 09/991,518, filed Nov. 16, 2001 (2 parts).
EFS File History of U.S. Appl. No. 10/561,711, filed Sep. 11, 2009 as of Aug. 26, 2011.
EFS File History of U.S. Appl. No. 10/561,711, filed Sep. 11, 2009 as of Apr. 21, 2012 (5 Parts).
EFS File History of U.S. Appl. No. 10/600,854, filed Jun. 20, 2003.
EFS File History of U.S. Appl. No. 10/821,621, filed Apr. 9, 2004.
EFS File History of U.S. Appl. No. 10/838,157, filed Apr. 30, 2004.
EFS File History of U.S. Appl. No. 10/871,368, filed Mar. 3, 2005 (3 parts).
EFS File History of U.S. Appl. No. 11/118,260, filed Apr. 29, 2005 (2 parts).
EFS File History of U.S. Appl. No. 11/147,622, filed Jun. 7, 2005.
EFS File History of U.S. Appl. No. 11/224,589, filed Sep. 12, 2005.
EFS File History of U.S. Appl. No. 11/228,416, filed Sep. 15, 2005.
EFS File History of U.S. Appl. No. 11/293,354, filed Dec. 2, 2005.
EFS File History of U.S. Appl. No. 11/412,476, filed Apr. 27, 2006 (2 parts).
EFS File History of U.S. Appl. No. 11/453,374, filed Jun. 15, 2006 (2 parts).
EFS File History of U.S. Appl. No. 11/539,648, filed Oct. 9, 2006.
EFS File History of U.S. Appl. No. 11/705,694, filed Feb. 12, 2007 (2 parts).
EFS File History of U.S. Appl. No. 11/841,588, filed Aug. 20, 2007 as of Aug. 4, 2010 (2 parts).
EFS File History of U.S. Appl. No. 11/841,588, filed Aug. 20, 2007.
EFS File History of U.S. Appl. No. 11/865,704, filed Oct. 1, 2007.
EFS File History of U.S. Appl. No. 11/966,787, filed Dec. 28, 2007 as of Nov. 19, 2010 (3 parts).
EFS File History of U.S. Appl. No. 11/966,787, filed Dec. 28, 2007.
EFS File History of U.S. Appl. No. 11/966,801, filed Dec. 28, 2007 as of Aug. 2, 2010 (3 parts).
EFS File History of U.S. Appl. No. 11/966,801, filed Dec. 28, 2007.
EFS File History of U.S. Appl. No. 12/028,024, filed Feb. 8, 2008.
EFS File History of U.S. Appl. No. 12/114,449, filed May 2, 2008.

(56) References Cited

OTHER PUBLICATIONS

EFS File History of U.S. Appl. No. 12/136,688, filed Jun. 10, 2008 as of Sep. 6, 2011.
EFS File History of U.S. Appl. No. 12/136,688, filed Jun. 10, 2008 as of Jul. 22, 2010 (3 parts).
EFS File History of U.S. Appl. No. 12/136,688, filed Jun. 10, 2008 as of Apr. 11, 2012 (5 Parts).
EFS File History of U.S. Appl. No. 12/183,007, filed Jul. 30, 2008 as of Nov. 7, 2011.
EFS File History of U.S. Appl. No. 12/183,007, filed Jul. 30, 2008 as of Aug. 9, 2011.
EFS File History of U.S. Appl. No. 12/183,007, filed Jul. 30, 2008 as of Nov. 9, 2010.
EFS File History of U.S. Appl. No. 12/282,343, filed Feb. 19, 2009 as of Jan. 26, 2012.
EFS File History of U.S. Appl. No. 12/329,504, filed Dec. 5, 2008 as of Aug. 16, 2011.
EFS File History of U.S. Appl. No. 12/329,518, filed on Dec. 5, 2008.
EFS File History of U.S. Appl. No. 12/464,686, filed May 12, 2009.
EFS File History of U.S. Appl. No. 12/464,868, filed May 12, 2009.
EFS File History of U.S. Appl. No. 12/638,860, filed Dec. 15, 2009 as of Mar. 9, 2012 (3 Parts).
EFS File History of U.S. Appl. No. 12/720,557, filed Mar. 9, 2010 as of Dec. 9, 2011.
EFS File History of U.S. Appl. No. 13/052,827, filed Mar. 21, 2011 as of Jan. 3, 2012.
EFS File History of U.S. Appl. No. 13/052,827, filed Mar. 21, 2011 as of Sep. 19, 2011.
Elliot et al., "Proteasome Inhibition: A New Anti-Inflammatory Strategy", J. Mol. Med., 81:235-245 (2003), Springer-Verlag.
Elliott et al., "The Proteasome: A New Target for Novel Drug Therapies", American Journal of Clinical Pathology, 116(5):637-646 (2001).
Endo et al., "Total Synthesis of Salinosporamide A", J. Am. Chem. Soc., 127(23):8298-8299 and Supporting Information S1-S23 (2005).
Erba et al., "Mode of Action of Thiocoraline, a Natural Marine Compound with Anti-Tumour Activity", British Journal of Cancer, 80(7):971-980 (1999).
Escuyer et al., "Anthrax Protective Antigen Interacts with a Specific Receptor on the Surface of CHO-K1 Cells", Infect. Immun., 59(10):3381-3386 (1991).
Faulkner, D.J., "Marine Natural Products", Nat. Prod. Rep., 18(1):1-49 (2001).
Feling et al., "Salinosporamide A: A Highly Cytotoxic Proteasome Inhibitor from a Novel Microbial Source, A Marine Bacterium of the New Genus Salinospora", Angew. Chem. Int. Ed. (2003), 42(3):355-357 Wiley-VCH Verlag GmbH & Co. KGaA, Weinheim, Germany.
Fenical et al., "Discovery and Development of the Anticancer Agent Salinosporamide A (NPI-0052)", Bioorganic & Med. Chem., 17:2175-2180 (2009).
Fenical et al., "Marine Microorganisms as a Biomedical Source: Are They Unculturable or Uncultured?", PowerPoint Presentation, Center for Marine Biotechnology and Biomedicine (2002). 23 pages, Scripps Institution of Oceanography. University of California San Diego.
Fenical et al., "Marine Microorganisms as a Developing Resource for Drug Discovery", Pharmaceutical News, 9:489-494 (2002).
Fenical et al., "Salinospora, a Major New Marine Actinomycete Taxon for Drug Discovery", Powerpoint Presentation, Center for Marine Biotechnology and Biomedicine (Jun. 24, 2001).
Fenical et al., "Salinospora, a Major New Marine Actinomycete Taxon for Drug Discovery", PowerPoint Presentation, Center for Marine Biotechnology and Biomedicine (2001), 37 pages, Scripps Institution of Oceanography, University of California, San Diego.
Fenical W., "Chemical Studies of Marine Bacteria: Developing a New Resource", Chem. Rev. (1993), 93:1673-1683, American Chemical Society.
Fenical W., "New Pharmaceuticals from Marine Organisms", Marine Biotechnology (1997), 15:339-341, Elsevier Science Ltd.
Fenteany et al., "Lactacystin, Proteasome Function, and Cell Fate", J. Biol. Chem., 273(15):8545-8548 (1998).
Fenteany et al., "Inhibition of Proteasome Activities and Subunit-Specific Amino-Terminal Threonine modification by Lactacystin", Science, 268:726-731 (1995).
Fernandez-Chimeno et al., "IB-96212, A Navel Cytotoxic Macrolide Produced by a Marine Micromonospora", The Journal of Antibiotics, 53(5):474-478 (2000).
Fingl et al., "General Principals", The Pharmaceutical Basis of Therapeutics, 5th Ed., (Goodman et al. Eds., 1975), MacMillan Publishing Co. Inc., New York, Chapter 1:1-46.
Folkman J., "Angiogenesis-Dependent Diseases", Seminars in Oncology, 28:536-542 (2001).
Folkman J., "Tumor Angiogenesis", Adv. Cancer Res., 43:175-203 (1985).
Fukuchi et al., "Direct proteasome inhibition by c/asto-lactacystin 13-lactone permits the detection of ubiquitinated p21 in ML-1 Cells", Biochem. Biophys. Acta, 1451:206-210 (1999).
Gale et al. (Eds.), The Molecular Basis of Antibiotic Action, 2nd ed., John Wiley and Sons, London (1981) Table of Contents, pp. 1-13.
Gantt et al., "Proteasome Inhibitors Block Development of Plasmodium SPP", Antimicrobial Agents and Chemotherapy, 42(10):2731-2738 (1998).
Geier et al., "A Giant Protease with Potential to Substitute for Some Functions of the Proteasome", Science, 283:978-981 (1999).
Gennaro A.R. (Ed.), Remington's Pharmaceutical Sciences, 17th Ed., Mack Publishing Co., Easton, PA, (1985), Table of Contents, pp. 5.
Gennaro A.R. (Ed.), Remington's Pharmaceutical Sciences, 18th Ed., Mack Publishing Co., Easton, PA (1990), Table of Contents, pp. 5.
Giannangeli et al., "Effect of Modifications of the Alkylpiperazine Moiety of Trazodone on SHT2A and a1 Receptor Binding Affinity", J. Med. Chem., 42(3):336-45 (1999).
Giovannoni S., "Oceans of Bacteria", Nature, 430:515-16 (2004).
Goldberg and Rock, "Not Just Research Tools—Proteasome Inhibitors Offer Therapeutic Promise", Nature Medicine, 8(4):338-340 (2002), Nature Publishing Group.
Golub et al., "Molecular Classification of Cancer: Class Discovery and Class Prediction by Gene Expression Monitoring", Science, 286:531-537 (1999).
Goodfelllow and O'Donnell, "Search and Discovery of Industrially-Significant Actinomycetes", In S. Baumberg et al. (Ed.) Microbial Products: New Approaches, Society for General Microbiology Symposium (1989), 44:343-383, Cambridge University Press.
Goodfellow and Williams, "Ecology of Actinomycetes", Ann. Rev. Microbial., 37:189-216 (1983), Annual Reviews Inc.
Goodfellow et al., "Actinomycetes in Biotechnology", Search and Discovery of New Antibiotics, Okami, et al., eds., Academic Press, San Diego, (1988) Chapter 2:33-67.
Goodfellow et al., "Ecology of Actinomycestes", Ann. Rev. Microbial., 37:189-216 (1983).
Grant et al., "Intracellular Mechanisms Involved in Basement Membrane Induced Blood Vessel Differentiation In Vitro", In Vitro Cell Dev. Biol., 27A:327-36 (1991).
Grosios et al., "Angiogenesis Inhibition by the Novel VEGF Receptor Tyrosine Kinase Inhibitor; PTK787/ZK222584, Causes Significant Anti-Arthritic Effects in Models of Rheumatoid Arthritis", Inflamm. Res., 53: 133-142 (2004).
Hanna et al., "On the Role of Macrophages in Anthrax", Proc. Natl. Acad. Sci. USA, 90:10198-10201 (1993).
Hardt et al., "Neomarinone, and New Cytotoxic Marinone Derivatives, Produced by a Marine Filamentous Bacterium (Actinomycetales)," Tetrahedron Letters, 41(13):2073-2076.
Harker et al., "Multidrug Resistance in Mitoxantrone-Selected HL-60 Leukemia Cells in the Absence of P-Giycoprotein Overexpression", Cancer Res., 49(16):4542-4549 (1989).
He et al., "Lomaiviticins A and B, Potent Antitumor Antibiotics from Micromonospora lomaivitiensis", J. Am. Chem. Sci., 123:5362-5363 (2001), American Chemical Society.

(56) References Cited

OTHER PUBLICATIONS

Helmke and Weyland, "*Rhodococcus marinonascens* sp. nov., an Actinomycete from the Sea", International Journal of Systematic Bacteriology, 34(2):127-138 (1984), International Union of Microbiological Societies.
Hideshima et al., "NF-KB as a Therapeutic Target in Multiple Myeloma", J. Biol. Chem., 277(19):16639-16647 (2002).
Higuchi et al., "Pro-Drugs as Novel Delivery Systems", vol. 14, A.C.S. Symposium Series American Chemical Society, Atlantic City, NJ., Sep. 10, 1974, (1975) Table of Contents, pp. 3.
Hogan et al., "Proteasome Inhibition by a Totally Synthetic /3-Lactam Related to Salinosporamide A and Omuralide", J. Am. Chem. Soc., 127(44):15386-15387 (2005).
Hopwood et al., "Genetic Manipulation of Streptomyces Polyketide Synthase Genes for Novel Secondary Metabolite Production", FEMS Microbiology Reviews, 16:233-234 (1995).
Horan A. C., "Aerobic Actinomycetes: A Continuing Source of Novel Natural Products", In V.P Gullo (Ed.) The Discovery of Natural Products with Therapeutic Potential (1994), 1-30, Butterworth-Heinemann, Boston.
Hull et al., "Antiangiogenic Agents Are Effective Inhibitors of Endometriosis", J. Clinical Endocrinology Metabolism, 88:2889-2899 (2003).
International Preliminary Report on Patentability (Chapter II) dated Aug. 6, 2010 for International Application No. PCT/US2009/043644, International Filing Date: May 12, 2009.
International Preliminary Report on Patentability dated Aug. 24, 2004 in International Application No. PCT/US2001/043758, International Filing Date: Nov. 16, 2001.
International Preliminary Report on Patentability dated Feb. 12, 2008 in International Application No. PCT/US2006/031314, International Filing Date: Aug. 10, 2006.
International Preliminary Report on Patentability dated Jan. 23, 2007 in International Application No. PCT/US2005/014846, International Filing Date: Apr. 29, 2005.
International Preliminary Report on Patentability dated Jan. 3, 2006 in International Application No. PCT/US2004/019543, International Filing Date: Jun. 18, 2004.
International Preliminary Report on Patentability dated Jun. 14, 2007 in International Application No. PCT/US2005/044091, International Filing Date: Dec. 2, 2005.
International Preliminary Report on Patentability dated Jun. 14, 2007 in International Application No. PCT/US2005/043668, International Filing Date: Dec. 2, 2005.
International Preliminary Report on Patentability dated Mar. 14, 2005 in International Application No. PCT/US2004/019453, International Filing Date: Jun. 18, 2004.
International Preliminary Report on Patentability dated Mar. 18, 2008 in International Application No. PCT/US2006/035196, International Filing Date: Sep. 8, 2006.
International Preliminary Report on Patentability dated May 6, 2008 in International Application No. PCT/US2006/043277, International Filing Date: Nov. 6, 2006.
International Preliminary Report on Patentability dated Nov. 19, 2009 in International Application No. PCT/US2008/062553, International Filing Date: May 2, 2008.
International Preliminary Report on Patentability dated Oct. 11, 2006 in International Application No. PCT/US2005/012218, International Filing Date: Apr. 11, 2005.
International Preliminary Report on Patentability dated Oct. 30, 2007 in International Application No. PCT/US2006/0161 04, International Filing Date: Apr. 27, 2006.
International Search Report and Written Opinion (corrected version) dated Jul. 8, 2005 in International Application No. PCT/US2004/019543, International Filing Date: Jun. 18, 2004.
International Search Report and Written Opinion dated Aug. 3, 2007 in International Application No. PCT/US2006/035196, International Filing Date: Sep. 8, 2006.
International Search Report and Written Opinion dated Dec. 29, 2006 in International Application No. PCT/US2005/014846, International Filing Date: Apr. 29, 2005.
International Search Report and Written Opinion dated Feb. 27, 2007 in International Application No. PCT/US06/016104, International Filing Date: Apr. 27, 2006.
International Search Report and Written Opinion dated Jan. 10, 2007 in International Application No. PCT/US2006/031314, International Filing Date: Aug. 10, 2006.
International Search Report and Written Opinion dated Jul. 12, 2006 in International Application No. PCT/US2005/044091, International Filing Date: Dec. 2, 2005.
International Search Report and Written Opinion dated May 12, 2006 in International Application No. PCT/US2005/043668, International Filing Date: Dec. 2, 2005.
International Search Report and Written Opinion dated Nov. 15, 2005 in International Application No. PCT/US2005/012218, International Filing Date: Apr. 11, 2005.
International Search Report and Written Opinion dated Nov. 27, 2007 in International Application No. PCT/US2006/043277, International Filing Date: Nov. 6, 2006.
International Search Report and Written Opinion dated Nov. 29, 2004 in International Application No. PCT/US2004/019453, International Filing Date: Jun. 18, 2004.
International Search Report and Written Opinion dated Oct. 19, 2005 in International Application No. PCT/US2005/012113, International Filing Date: Apr. 11, 2005.
International Search Report and Written Opinion dated Sep. 28, 2009 for International Application No. PCT/US2009/043644, International Filing Date: May 12, 2009.
International Search Report and Written Opinion dated Jan. 29, 2009 for corresponding International Application No. PCT/US2008/062553 International Filing Date: May 2, 2008.
International Search Report dated Aug. 2, 2002 in International Application No. PCT/US01/043758, International Filing Date: Nov. 16, 2001.
Jensen and Fenical, "Marine Microorganisms and Drug Discovery: Current Status and Future Potential", In N. Fusetani (Ed.) Drugs from the Sea (2000), 6-29, S. Karger AG, Basel.
Jensen and Fenical, "Strategies for the Discovery of Secondary Metabolites from Marine Bacteria: Ecological Perspectives", Annu. Rev. Microbial., 48:559-584 (1994), Annual Reviews Inc.
Jensen et al., "Distribution of Actinomycetes in Near-Shore Tropical Marine Sediments," Applied ana Environmental Microbiology, 57(4):1102-1108 (1991), American Society for Microbiology.
Jensen et al., "The Relative Abundance and Seawater Requirements of Gram-Positive Bacteria in Near-Shore Tropical Marine Samples", Microbial Ecology, 29(3):249-257 (1995).
Jia et al., "The Proteasome Inhibitor NPI-0052 in Combination with Bortezomib Induces Antitumor Activity in Waldenstrom Macroglobulinemia", Blood ASH Annual Meeting Abstracts, 108: Abstract 4746 (2006).
Jiang et al., "Antinoflavoside, A Novel Flavonoid-Like Glycoside Produced by a Marine Bacterium of the Genus *Streptomyces*", Tetrahedron Letters, 38(29):5065-5068 (1997).
Johnson et al., "Relationships between drug activity in NCI preclinical in vitro and in vivo models and early clinical trials", British J. Cancer, 84(11 ):1424-1431 (2001).
Joseph et al., "Laboratory Cultivation of Widespread and Previously Uncultured Soil Bacteria", Applied and Environmental Microbiology, 69(12):7210-7215 (2003), American Society for Microbiology.
Joshi A., "Microparticulates for Ophthalmic Drug Delivery", J. Ocul. Pharmacol., 10:29-45 (1994).
Kalns et al., "Delayed Treatment With Doxycycline Has Limited Effect on Anthrax Infection in BLK57/B6 Mice", Biochem. Biophys. Res. Commun., 297:506-509 (2002).
Kains et al., TNF Receptor 1, IL-1 Receptor, and iNOS Genetic Knockout Mice Are Not Protected from Anthrax Infection, Biochem. Biophys. Res. Commun., 292:41-44 (2002).
Kerr et al., "Marine Natural Products as Therapeutic Agents", Exp. Opinion on Therapeutic Patents, 9(9):1207-1222 (1999).
Khanbolooki et al., "Novel NFKB inhibitors NPI-1342/NPI-1387 and proteasome inhibitor NPI-0052 overcome resistance of pan-

(56) References Cited

OTHER PUBLICATIONS creatic carcinoma to rhTRAIL", Nereus Pharmaceuticals, Inc., (Apr. 2, 2006), abstract 780 for presentation at the American association of Cancer Research Annual Meeting held on Apr. 2, 2006 in Washington, D.C., 1 page.
Kim et al., "Sensitizing Anthrax Lethal Toxin-Resistant Macrophages to Lethal Toxin-Induced Killing by Tumor Necrosis Factor", J. Biol. Chem., 278:7413-7421 (2003).
King et al., "How Proteolysis Drives the Cell Cycle", Science, 274:1652-1659 (1996).
Kisselev et al., "Importance of the Different Proteolytic Sites of the Proteasome and the Efficacy of Inhibitors Varies with the Protein Substrate", J. Bio. Chem., 281 (13): 8582-8590 (2006).
Kisselev et al., "Proteasome Inhibitors: From Research Tools to Drug Candidates", Chem. Biol., 8:739-758 (2001).
Koch et al., "16S Ribosomal DNA Analysis of the Genera Micromonospora, Actinoplanes, 142 Catellatospora, Catenuloplanes, Dactylosporangium, and Pillimelia and Emendation or the Family Micromonosporaceae", Intl. Journal of Systematic Bacteriology, 46(3):765-768 (1996).
Kozlowski et al., "Lactacystin Inhibits Cathepsin A Activity in Melanoma Cell Lines", Tumor Biol., 22:211-215 (2001).
Lacy et al., "Mapping the Anthrax Protective Antigen Binding Site on the Lethal and Edema Factors", J. Biol. Chem., 277:3006-3010 (2002).
Lala et al., "Role of nitric oxide in tumor progression: lessons from experimental tumors", Cancer Metastasis Rev., 17(1):91-106 (1998).
Lam et al., "Isolation of a Bromo Analog of Rebeccamycin From Saccharothrix Aerocolonigenes", J. Antibiotics, 44(9):934-939 (1991).
Lam et al., "Production, Isolation and Structure Determination of Novel Fluoroindolocarbazoles from Saccharothrix aerocolonigenes A TCC 39243", J. Antibiotics, 54(1):1-9 (2001).
Lawley et al., "Induction of Morphologic Differentiation of Endothelial Cells in Culture", J. Investigative Dermatology, 93(2 Supplement):59S-61S (1989).
Lenz et al., "Clinical Update: Proteasome Inhibitors in Solid Tumors", Cancer Treatment Reviews, 29 (1 Supplement):41-48 (2003).
Lightcap et al., "Proteasome Inhibition Measurements Clinical Application", Clin. Chem., 46(5):673-683 (2000).
Lin et al., "Cytotoxic Effects of Anthrax Lethal Toxin on Macrophage-Like Cell Line J774A.1", Curr. Microbiol., 33:224-227 (1996).
Liu et al., "Angiogenesis Inhibitors May Regulate Adiposity", Nutr. Rev., 61:384-387 (2003).
Liu et al., "Precursor Supply for Polyketide Biosynthesis: The Role of Crotonyl-GoA Reductase", Metab. Eng., 3:40-48 (2001).
Macherla et al., "Structure-Activity Relationship Studies of Salinosporamide A (NPI-0052), a Novel Marine Derived Proteasome Inhibitor", J. Med. Chem., 48(11):3684-3687 (2005).
Manam et al., "Stereoselective Enzymatic Reduction of Keto-Salinosporamide to(-)-salinosporamide A (NPI-0052)", Tetra. Lettr., 48:2537-2540 (2007).
Manam et al., "Leaving Groups Prolong the Duration of 20S Proteasome Inhibition and Enhance the Potency of Salinosporamide", J. Med. Chem., 51 (21):6711-6724 (2008).
Manchand et al., "Syntheses of the Anti-AIDS Drug 2',3'-Dideoxycytidine from Cytidine", *J. Org. Chem.*, 57:3473-3478 (1992).
Mayer et al., "Efficacy of a Novel Hydrogel Formulation in Human Volunteers," Ophthalmologica, 210(2)101-103 (1996).
Mayer et al., "Marine Pharmacology in 1999: Antitumor and Cytotoxic Compounds", Anticancer Res., 21:2489-2500 (2001).
McMurry, John, Organic Chemistry, 5th ed., Brooks/Cole, Pacific Grove, CA. (2000), Chapter 11.5, pp. 398-408.
Meng et al., "Eponemycin Exerts its Antitumor Effect Through the Inhibition of Proteasome Function", Cancer Res., 59(12):2798-2801 (1999).
Meng et al., "Epoxomicin, a Potent and Selective Proteasome Inhibitor, Exhibits In Vivo Anti-Inflammatory Activity", Proc. NatL Acad. Sci. USA, 96:10403-10408 (1999).

Merriam-Webster Online Dictionary, "Heteroatom", 2010, Merriam-Webster Online, accessed Jun. 16, 2010, http://merriam-webster.com/dictionary/heteroatom.
Min et al., "Urokinase Receptor Antagonists Inhibit Angiogenesis and Primary Tumor Growth in Syngeneic Mice", Cancer Res., 56(10):2428-2433 (1996).
Mincer et al., "Widespread and Persistent Populations of a Major New Marine Actinomycete Taxon in Ocean Sediments", Applied and Environmental Microbiology, 68(10):5005-5011 (2002).
Mogridge et al., "Stoichiometry of Anthrax Toxin Complexes", Biochemistry, 41:1079-1082 (2002).
Momose et al., "2(3H)-and 2(5H)-Furanones. VII. Chirality Transfer on the Tetronic Acid Templates", Heterocycles, 51(6):1321-1343 (1999).
Moore B.S., "Biosynthesis of Marine Natural Products: Microorganisms and Macroalgae", Nat. Prod. Rep., 16(6):653-674 (1999).
Moran et al., "Evidence for Indigenous Streptomyces Populations in a Marine Environment Determined with a 16S rRNA Probe", Applied and Environmental Microbiology, 61 (10):3695-3700 (1995).
Mordenti et al., "Intracular Pharmacokinetics and Safety of a Humanized Monoclonal Antibody in Rabbits after Intravitreal Administration of a Solution or a PLGA Microsphere Formulation", Toxicol. Sci., 52(1 ): 101-106 (1999).
Mousa et al., "Angiogenesis Inhibitors: Current & Future Directions", Current Pharmaceutical Design, 10:1-9 (2004).
Mulholland et al., "A Concise Total Synthesis of Salinosporamide A", Org. Biomol. Chem., 4: 2845-6 (2006).
Murray, J. Clifford (Ed.), Angiogenesis Protocols (Methods in Molecular Medicine), Humana Press, Totowa, NJ. (2001) Table of Contents, pp. 4.
Mutomba et al., "Inhibition of Proteasome Activity Blocks Cell Cycle Progression at Specific Phase Boundaries in African Trypanosomes", Mol. Biochem. Parasitology, (1997) 90:491504 (1997).
NCBI website, sequence for AB242910, http://www.ncbi.nlm.nih.gov/entrezJviewer.fcgi?db=nucleotide&val=124300751, down loaded Feb. 15, 2007, 2 pages.
NCBI website, sequence for EF105548, http://www.ncbi.nlm.nih.gov/entrez/viewerfcgi?db=nucleotide&val=118640518, downloaded Feb. 15, 2007, 2 pages.
NCBI website, Sequence for EF191171, http://www.ncbi.nlm.nih.gov/entrez/viewer.fcgi?db=nucleotide&val=124014014, downloaded Feb. 15, 2007, 2 pages.
Nesterneko et al., "*Rhodococcus luteus* nom. nov., and *Rhodococcus marls* nom. nov.", Int'l Journal of Systematic Bacteriology, 32(1):1-14 (1982).
Nicholson D.W., "ICE/CEO 3-Like Proteases as Therapeutic Targets for the Control of Inappropriate Apoptosis", Nat. Biotechnology, 14:297-301 (1996).
Nicolaus B.J.R., "Symbiotic Approach to Drug Design", In F. Gross (Ed.) Decision Making in Drug Research (1983), 173-186, Raven Press, New York.
Nicosia et al., "Growth of Microvessels in Serum-Free Matrix Culture of Rat Aorta: A Quantitative Assay of Angiogenesis In Vitro", Laboratory Investigation, 63(1):115-122 (1990).
Nolan et al., "Isolation and Screening of Actinomycetes", Actinomycetes in Biotechnology, Chapter 1:1-32 (1988).
O'Donnel, A.G., "Recognition of Novel Actinomycetes", Actinomycetes in Biotechnology, Academic Press, Chapter 3:69-88 (1988).
Ogiso, Yasunari, et al., "Proteosome Inhibition Circumvents Solid Tumor Resistance to Topoisomerase 11-directed Drugs", Cancer Research, 60, 2429-2434 (2000).
Oikawa et al., "Angiogenic Factor of a Rat Mammary Tumor Cell Line (RMT-1) (I). Secretion of Two Distinct Angiogenic Factors into Serum-Free Conditioned Medium by RMT-1 Cells", Cancer Letters 59:57-66 (1991).
Okami and Hotta, "Search and Discovery of New Antibiotics", In M. Goodfellow et al. (Ed.) Actinomycetes in Biotechnology, 33-67 (1988), Academic Press, San Diego.
Okami Y., The Search for bioactive Metabolites from Marine Bacteria, Journal of Marine Biotechnology, 1:59-65 (1993).

(56) References Cited

OTHER PUBLICATIONS

Omura et al., "Lactacystin, A Novel Microbial Metabolite, Induces Neuritogenesis of Neuroblastoma Cells", J. Antibiotics, 44(1):113-116 (1991).
O'Neil et al. eds., "The Merck Index", 13th Ed. 2001, Merck Research Laboratories, Whitehouse Station N.J., pp. THER-5-THER-7.
Online URL:http://aidsinfo.nih.gov/DrugsNew/DrugDetaiiNT.aspx?MenuItem=Drugs&Search=On&int_id=244: pp. 1-2.
Online URL:http://en.wikipedia.org/wiki/Myeloma; pp. 1-8.
Online URL:http://en.wikipedia.org/wiki/Sarcoma; pp. 1-2.
Online URL:http://lweb.archive.org/web/20060117081111/hivheP.temPdomainname.com/hiv and aids/norvir effects . . . Nov. 22, 2010. 1 page.
Online www.netdoctor.co.uk "Isoniazid: Treatment of Tuberculosis", [accessed on Apr. 8, 2008]pp. 1-2.
Ostrowska et al., "Lactacystin, A Specific Inhibitor of the Proteasome, Inhibits Human Platelet Lysosomal Cathepsin A-like Enzyme", Biochem. Biophys. Res. Commun., 234:729-732 (1997).
Ostrowska et al., "Separation of Cathepsin A-like Enzyme and the Proteasome: Evidence that Lactacystin/(3-Lactone is not a Specific Inhibitor of the Proteasome", Int. J. Biochem. Cell Biol., 32:747-757 (2000).
Otoguro et al., "An Integrated Method for the Enrichment and Selective Isolation of *Actinokineospora* spp. In Soil and Plant Litter, Journal of Applied Microbiology, 91:118-130 (2001),"The Society for Applied Microbiology.
Pagano et al., "Role of the Ubiquitin-Proteasome Pathway in Regulating Abundance of the Cyclin-Dependent Kinase Inhibitor p27", Science, 269(5224):682-685 (1995).
Page, Roderic D.M., "TreeView: An Application to Display Phylogenetic Trees on Personal Computers", Computer Applications in the Biosciences, 12:357-358 (1996).
Painter R.B., "Inhibition of DNA Replicon Initiation by 4-Nitroquinoline 1-Oxide, Adriamycin, and Ethyleneimine", Cancer Res., 38(12):4445-4449 (1978).
Palayoor et al., "Constitutive Activation of IkB Kinase a and NF-kB in Prostate Cancer Cells is Inhibited by Ibuprofen", Oncogene, 18:7389-7394 (1999).
Peckham et al. (Eds. ), "The Oxford Textbook of Oncology", Oxford University Press, Oxford (1995) vol. 1:447-453.
Pieters et al., "Microbiology: Chemical Warfare and Mycobacterial Defense", Science, 302:1900-1902 (2003).
Plunkett et al., "Methods in Laboratory Investigation: An In Vivo Quantitative Angiogenesis Model Using Tumor Cells Entrapped in Alginate", Laboratory Investigation, 0-517 (1990).
Prudhomme et al., "Marine Actinomycetes: A New Source of Compounds against the Human Malaria Parasite", Plos One, 3(6):1-8 (2008).
Qureshi et al., "The Proteasome as a Lipopolysaccharide-Binding Protein in Macrophages: Differential Effects of Proteasome Inhibition on Lipopolysaccharide-Induced Signaling Events", J. Immunol., 171(3):1515-1525 (2003).
Rappe et al., "Cultivation of the Ubiquitous SAR11 Marine Bacterioplankton Clade", Nature, 418:630-633 (2002).
Reddy et al., "A Simple Stereocontrolled Synthesis of Salinosporamide A", J. Am. Chem. Soc., 126:6230-6231 (2004).
Reed et al., "Salinosporamides D-J from the Marine Actinomycete Salinispora tropica, Bromosolinosporamide, and Thioester Derivatives Are Potent Inhibitors of the 20S Proteasome", J. Nat. Prod., 70: 269-276 (2007).
Riva S., "Biocatalytic Modification of Natural Products", Curr. Opin. Chem. Biol., 5:106-111 (2001).
Rivieccio G., "Il Fonda Agli Oceani Potenti Antibiotici e Anticancro", Newton (2003), 1 pp.
Roccaro et al., "Dual Targeting of the Proteasome Regulates Survival and Homing in Waldenstrom Macroglobulinemia", Blood, 111(9):4752-4763 (2008).
Roche E.B. (Ed.), "Bioreversible Carriers in Drug Design: Theory and Application", Pergamon Press, Elmsford, NY (1987), pp. 14-21.
Rockwell et al., "Proteasome Inhibition in Neuronal Cells Induces a Proinflammatory Response Manifested by Upregulation of Cyclooxygenase-2, Its Accumulation as Ubiquitin Conjugates, and Production of the Prostaglandin PGE2", Arch. Biochem. and Biophysics, 374(2):325-333 (2000).
Romero et al., "Thiocoraline, a New Depsipeptide with Antitumor Activity Produced by a Marine Micromonospora", The Journal of Antibiotics, 50(9):734-737 (1997).
Rubanyi, Gabor M., "Angiogenesis in Health and Disease: Basic Mechanisms and Clinical Applications", Marcel Dekker, New York, NY (1999) pp. 6 Content Pages Only.
Ruiz et al., "The Proteasome Inhibitor NPI-0052 is a More Effective Inducer of Apoptosis than Bortezomib in Lymphocytes from Patients with Chronic Lymphocytic Leukemia", Mol. Cancer Ther., 5(7):1836-1843 (2006).
Sapi et al., "Simple and Condensed 13-Lactam. Part 32. Base- and Acid-Catalyzed Ring Expansions of 3-Substituted 4-Acetylazetidin-2-ones and Related Compounds". Collect. Czech. Chem. Commun., 64(2):190-202 (1999).
Saravanan et al., "A Short, Stereocontrolled, and Practical Synthesis of a-Methylomuralide, a Potent Inhibitor of Proteasome Function", J. Org. Chem., 68(7):2760-2764 (2003).
Sausville et al., "Contributions of human tumor xenografts to anticancer drug development", Cancer Res., 66(7): 3351-3354 (2006).
Schiewe, H. (Reprint) Haustedt et al., "Rational approaches to natural-product-based drug design", Curr. Opin. Drug Disc. Devel., 9(4):445-462 (2006).
Schnaper et al., "Plasminogen Activators Augment Endothelial Cell Organization In Vitro by Two Distinct Pathways", J. Cell. Physiol., 165:107-118 (1995).
Shadomy et al., "Antimycotic and Antirickettsial", Antibiotics, Chemotherapeutics, and Antibacterial Agents for Disease Control, Martin Grayson (Ed.) John Wiley and Sons, New York (1982) 371-395.
Shimada et al., "Contributions of Mitogen-Activated Protein Kinase and Nuclear Factor Kappa B to N-(4-hydroxyphenyl) Retinamide-Induced Apoptosis in Prostate Cancer Cells", Molecular Carcinogenesis, 35(3):127-137 (2002).
Shoemaker R., "The NCI60 Human Tumour Cell Line Anticancer Drug Screen", Nature Reviews Cancer, 6:813-823 (2006).
Silva-Jardim et al., "The Leishmania Chagasi Proteasome: Role in Promastigotes Growth and Amastigotes Survival within Murine Macrophages", Acta Tropica, 91:121-130 (2004).
Silverman R.B., The Organic Chemistry of Drug Design and Drug Action, Academic Press, San Diego, (1992) 19-21.
Stach et al., "New Primers for the Class Actinobacteria: Application to Marine and Terrestrial Environments," Environmental Microbiology, 5(10):828-841 (2003), Society for Applied Microbiology and Blackwell Publishing Ltd.
Stach et al., "Statistical Approaches for Estimating Actinobacterial Diversity in Marine Sediments", Applied and Environmental Microbiology, 69(10):6189-6200 (2003), American Society for Microbiology.
Stackebrandt et al., "Proposal for a New Hierarchic Classification Systems, Actinobacteria classis Nov.", Int. J. of Syst. Bacterial., 47(2):4 79-491 (1997).
Stackebrandt et al., "Taxonomic Note: A Place for DNA-DNA Reassociation and 16S Rrna Sequence Analysis in the Present Species Definition in Bacteriology", Int. J. of Syst. Bacterial., 44(4):846-849 (1994).
Stadler et al., "Cinnabaramides A-G: Analogues of Lactacystin and Salinosporamide from a Terrestrial Streptomycete", J. Nat. Prod. 70(2):246-252 (2007).
Stanford et al., "Bortezomib Treatment for Multiple Myeloma", Ann. Pharmacother., 37:1825-1830 (2003).
Stella et al., (Ed.), "Prod rugs: Challenges and Rewards, Part 1", American Association of Pharma. Scientists, pp. 24 (2007).
Stinson et al., "Morphological and immunocytochemical characteristics of human tumor cell lines for use in a disease-oriented anticancer drug screen", Anticancer Res., 12(4):1035-53 (1992).
Streitwieser et al., Introduction to Organic Chemistry, 2nd ed., Macmillan Publishing Co. Inc., New York, NY (1981) pp. 169-171.

(56) References Cited

OTHER PUBLICATIONS

Sunwoo et al., "Novel Proteasome Inhibitor PS-341 Inhibits Activation of Nuclear Factor-kB, Cell 224 Survival, Tumor Growth, and Angiogenesis in Squamous Cell Carcinoma", C/in. Cancer Res., (2001) 7:1419-1428.
Suzuki et al., "Chemosensitization of Drug and Rituximab-Resistant Daudi B-NHL Clones to Drug-Induced Apoptosis by the Proteasome Inhibitor NPI-0052", Blood, (2005) 106:1521 abstract.
Tabuchi et al., "Application of 'Proteasome Tolerance' to Therapies for Neurodegenerative Disease", Alzheimer's and Dementia, 2(3) (1 Supplement):5628 (2006).
Tang et al., "Cloning and Hererologous Expression of the Epothilong Gene Cluster", Science, 287:640-642 (2000).
Tang et al., "Proteasome Activity is Required for Anthrax Lethal Toxin to Kill Macrophages", Infect. Immun., 67(6):3055-3060 (1999).
Tauchi et al., "Molecular Mechanisms of Resistance of Leukemia to Imatinib Mesylate", Leukemia Research, 28:39-45 (2004).
Thompson et al., "CLUSTAL W: improving the sensitivity of progressive multiple sequence alignment through sequence weighting, position-specific gap penalties and weight matrix choice", Nucleic Acids Research, 22(22):4673-4680 (1994).
Tomida, Akihiro et al., "Drug Resistance Pathways As Targets", Anticancer Drug Development, Academic Press, Chapter Five (2002).
Versalovic et al., "Distribution of repetitive DNA sequences in eubacteria and applicaticm to fingerprinting of bacterial genomes", Nucleic Acids Research, 19(24):6823-6831 (1991).
Vitale et al., "Anthrax lethal factor cleaves the N-terminus of MAPKKS and induces tyrosine/threonine phosphorylation of MAPKS in cultured macrophages", J. Applied Microbiology, 87:288 (1999).
Vitale et al., "Susceptibility of Mitogen-Activated Protein Kinase Kinase Family Members to Proteolysis by Anthrax Lethal Factor", Biochem. J., 352:739-745 (2000).
Voskoglou-Nomikos et al., "Clinical Predictive Value of the in Vitro Cell Line, Human Xenograft, and Mouse Allograft Preclinical Cancer Models", Clin. Cancer Res., 9:42274239 (2003).
Ward Bess B., "How Many Species of Prokaryotes are There?" Proc. Natl. Acad. Sci. USA, 99(16):10234-10236 (2002).
Watve et al., "How Many Antibiotics Are Produced by the Genus *Streptomyces*?", Arch. Microbial., 176:386-390 (2001), Springer-Verlag.
Weyland, H., "Actinomycetes in North Sea and Atlantic Ocean Sediments", Nature, 223:858 (1969).
Weyland, H., (Eds.), "Distribution of Actinomycetes on the Sea Floor", Actinomycetes Zbl. Bakt. Suppl., 11:185-193 (1981).
Wheelis et al., "On the Nature of Global Classification", Proc. Natl. Acad. Sci. USA, 89:2930-2934 (1992).
Williams et al., "New Cytotoxic Salinosporamides from the Marine Actinomycete Salinispora Tropica", J. Org. Chem., 70(16):6196-6203 (2005).
Woese Carl R., "Bacterial Evolution", Microbiological Rev., 51(2):221-271 (1987).
Yew et al., "Proteasome Inhibition by Lactacystin in Primary Neuronal Cells Induces Both Potentially Neuroprotective and Pro-Apoptotic Transcriptional Responses: a Microarray Analysis", J. Neurochem., 94(4):943-956 (2005).
Zaks A., "Industrial Biocatalysts", Curr. Opin. Chem. Biol., 5:130-136 (2001).
Zhang et al., "Postischemic (6 Hour) Treatment with Recombinant Human Tissue Plaminogen Activator and Proteasome Inhibitor PS-519 Reduces Infarction in a Rat Model of Embolic Focal Cerebral Ischemia", Stroke, 2926-2931 (2001).
Zheng et al., "Detection of Antitumor and Antimicrobial Activities in Marine Organism Associated Actinomycetes Isolated from the Taiwan Strait, China", FEMS Microbiology Letters, 188:87-91 (2000).

Cytotoxic activity of salinosporamide A (1) and dose response curve

Comp8 (units/ml)

| Sample | Wells | Sample # | OD | Mean Value | Ctr. Avg OD | % Survival | Concentration | IC50 |
|---|---|---|---|---|---|---|---|---|
| Co03 | C8 | 1 | 0.013 | 0.013 | 1.305 | 0.958 | 78.125 | 0.011 |
| Co04 | D8 | 2 | 0.044 | 0.044 | 1.305 | 3.335 | 19.531 | 0.011 |
| Co05 | E8 | 3 | 0.059 | 0.059 | 1.305 | 4.484 | 4.883 | 0.011 |
| Co06 | F8 | 4 | 0.105 | 0.105 | 1.305 | 8.011 | 1.221 | 0.011 |
| Co07 | G8 | 5 | 0.170 | 0.170 | 1.305 | 12.993 | 0.305 | 0.011 |
| Co08 | H8 | 6 | 0.304 | 0.304 | 1.305 | 23.266 | 0.076 | 0.011 |

Standards (mg/ml)

| Sample | Concentration | Back CalcConc | Wells | OD | Mean OD | % Survival | CV % | Ctr. Avg OD | IC50 |
|---|---|---|---|---|---|---|---|---|---|
| Sta03 | 31.250 | Range? | C12 | 0.413 | 0.413 | 31.621 | 0.0 | 1.305 | 0.828 |
| Sta04 | 7.813 | Range? | D12 | 0.542 | 0.542 | 41.510 | 0.0 | 1.305 | 0.828 |
| Sta05 | 1.953 | Range? | E12 | 0.557 | 0.557 | 42.660 | 0.0 | 1.305 | 0.828 |
| Sta06 | 0.488 | Range? | F12 | 0.760 | 0.760 | 58.222 | 0.0 | 1.305 | 0.828 |
| Sta07 | 0.122 | Range? | G12 | 1.287 | 1.287 | 98.620 | 0.0 | 1.305 | 0.828 |
| Sta08 | 0.031 | Range? | H12 | 1.615 | 1.615 | 123.764 | 0.0 | 1.305 | 0.828 |

Smallest standard value: 0.413
Largest standard value: 1.615

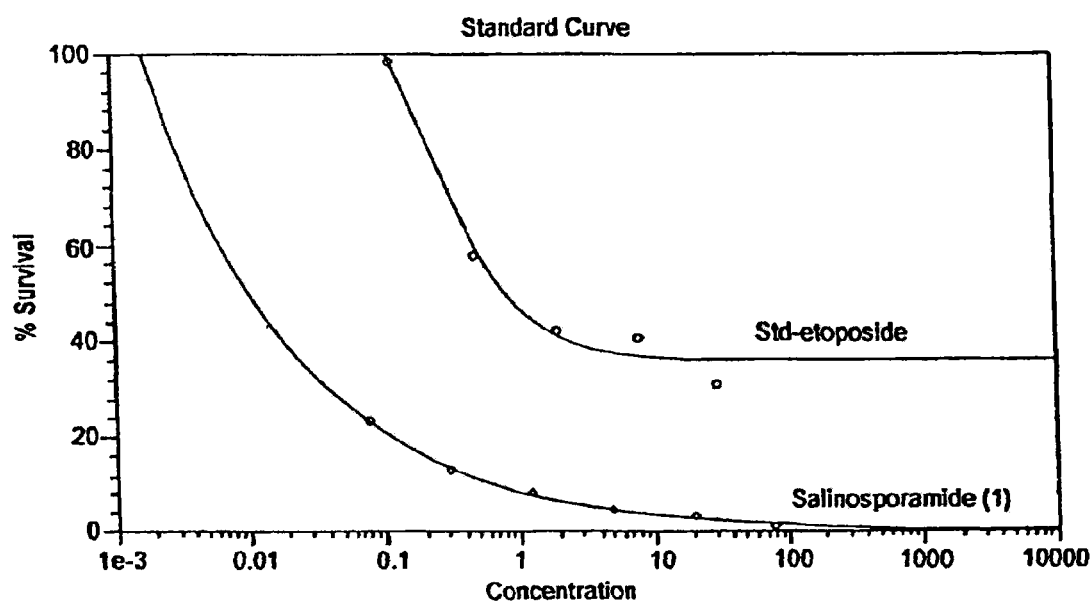

$y = ( (A - D)/(1 + (x/C)^B) ) + D$:

| | A | B | C | D | R^2 |
|---|---|---|---|---|---|
| ○ Comp.8 (Comp8: Concentration vs % Survival) | 2183.255 | 0.398 | 8.34e-7 | 0.073 | 0.997 |
| ○ Std (Standards: Concentration vs % Survival) | 133.236 | 1.227 | 0.192 | 36.119 | 0.993 |

FIG. 4

| Position 16S rDNA | Actinoplanes | Micromon-ospora | Dactylo-sporangium | Catellato-spora | Pilimelia | Catenulo-planes | Couchio-planes | Spirilli-planes | Verrucosi-spora | Marinospora |
|---|---|---|---|---|---|---|---|---|---|---|
| 207 | U | U | U | U | C | U | U | U | U | A |
| 219 | C | C | C | C | U | C | C | C | C | U |
| 279 | A | A | A | (A/U) | A | A | A | A | A | G |
| 366 | A | (A/G) | A | A | G | (G/A) | A | A | A | C |
| 467 | A | A | (G/A) | A | A | A | A | A | A | U |
| 468 | A | A | A | A | A | A | A | A | A | U |
| 546 | G | G | G | G | U | G | G | G | G | A |
| 615 | C | (G/C) | C | (U/C) | C | (C/U) | C | C | U | U |
| 1116 | C | C | (C/U) | C | C | C | C | C | C | U |
| 1456 | A | A | A | A | A | A | A | A | A | G |

FIG. 15

SALINOSPORAMIDES AND METHODS OF USE THEREOF

CROSS-REFERENCE TO RELATED APPLICATIONS

This application is a continuation application of U.S. application Ser. No. 15/655,739, now pending; which is a continuation application of U.S. application Ser. No. 14/794,468 filed Jul. 8, 2015, now issued as U.S. Pat. No. 9,713,607; which is a continuation application of U.S. application Ser. No. 14/139,692 filed Dec. 23, 2013, now issued as U.S. Pat. No. 9,078,881; which is a divisional application of U.S. application Ser. No. 13/477,364 filed May 22, 2012, now issued as U.S. Pat. No. 8,637,565; which is a continuation application of U.S. application Ser. No. 12/638,860 filed Dec. 15, 2009, now issued as U.S. Pat. No. 8,222,289; which is a continuation application of U.S. application Ser. No. 11/705,694 filed Feb. 12, 2007, now issued as U.S. Pat. No. 7,635,712; which is a continuation application of U.S. application Ser. No. 11/147,622 filed Jun. 7, 2005, now issued as U.S. Pat. No. 7,176,233; which is divisional application of U.S. application Ser. No. 10/838,157 filed Apr. 30, 2004, now issued as U.S. Pat. No. 7,176,232; which is a continuation-in-part application of U.S. application Ser. No. 10/600,854 filed Jun. 20, 2003, now issued as U.S. Pat. No. 7,179,834; which claims the benefit under 35 U.S.C. § 119(e) to U.S. Application Ser. No. 60/391,314 filed Jun. 24, 2002, now expired. The disclosure of each of the prior applications is considered part of and is incorporated by reference in the disclosure of this application.

STATEMENT REGARDING FEDERALLY SPONSORED RESEARCH OR DEVELOPMENT

This invention was made with government support under Grant No. CA44848 awarded by the National Institutes of Health, National Cancer Institute. The government has certain rights in the invention.

BACKGROUND OF THE INVENTION

Field of the Invention

The invention relates generally to anti-neoplastic agents, and more particularly to salinosporamides and their use as anti-neoplastic agents.

Background Information

Neoplastic diseases, characterized by the proliferation of cells not subject to the normal control of cell growth, are a major cause of death in humans. Clinical experience in chemotherapy has demonstrated that new and more effective cytotoxic drugs are desirable to treat these diseases. Indeed, the use of anti-neoplastic agents has increased due to the identification of new neoplasms and cancer cell types with metastases to different areas, and due to the effectiveness of antineoplastic treatment protocols as a primary and adjunctive medical treatment for cancer.

Since anti-neoplastic agents are cytotoxic (poisonous to cells) they not only interfere with the growth of tumor cells, but those of normal cells. Anti-neoplastic agents have more of an effect on tumor cells than normal cells because of their rapid growth. Thus, normal tissue cells that are affected by anti-neoplastic agents are rapidly dividing cells, such as bone marrow (seen in low blood counts), hair follicles (seen by way of hair loss) and the GI mucosal epithelium (accounting for nausea, vomiting, loss of appetite, diarrhea). In general, anti-neoplastic agents have the lowest therapeutic indices of any class of drugs used in humans and hence produce significant and potentially life-threatening toxicities. Certain commonly-used anti-neoplastic agents have unique and acute toxicities for specific tissues. For example, the *vinca* alkaloids possess significant toxicity for nervous tissues, while adriamycin has specific toxicity for heart tissue and bleomycin has for lung tissue.

Thus, there is a continuing need for anti-neoplastic agents that are effective in inhibiting the proliferation of hyperproliferative cells while also exhibiting $IC_{50}$ values lower than those values found for current anti-neoplastic agents, thereby resulting in marked decrease in potentially serious side effects.

SUMMARY OF THE INVENTION

The present invention is based on the discovery that certain fermentation products of the marine actinomycete strains CNB392 and CNB476 are effective inhibitors of hyperproliferative mammalian cells. The CNB392 and CNB476 strains lie within the family Micromonosporaceae, and the generic epithet Salinospora has been proposed for this obligate marine group. The reaction products produced by this strain are classified as salinosporamides, and are particularly advantageous in treating neoplastic disorders due to their low molecular weight, low $IC_{50}$ values, high pharmaceutical potency, and selectivity for cancer cells over fungi.

In one embodiment of the invention, there is provided compounds having the structure (I):

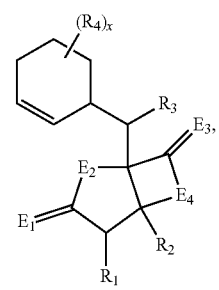

wherein:
R$_1$ to R$_3$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;
Each R$_4$ is independently alkyl, substituted alkyl, alkenyl, substituted alkenyl, alkynyl, substituted alkynyl, aryl, substituted aryl, cycloalkyl, substituted cycloalkyl;
E$_1$ to E$_4$ are each independently —O, —NR$_5$, or —S, wherein R$_5$ is —H or C$_1$-C$_6$ alkyl; and
x is 0 to 8.
In a further embodiment of the invention, there are provided compounds having the structure (II):

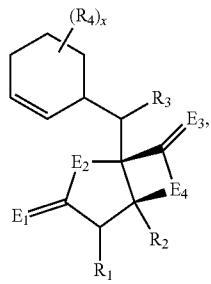

II wherein:

$R_1$ to $R_3$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

Each $R_4$ is independently alkyl, substituted alkyl, alkenyl, substituted alkenyl, alkynyl, substituted alkynyl, aryl, substituted aryl, cycloalkyl, substituted cycloalkyl;

$E_1$ to $E_4$ are each independently —O, —$NR_5$, or —S, wherein $R_5$ is —H or $C_1$-$C_6$ alkyl; and x is 0 to 8.

In another embodiment of the invention, there are provided compounds having the structure (III):

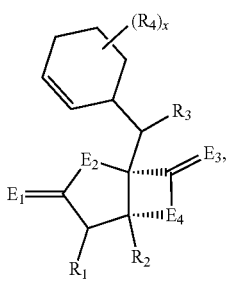

III wherein:

$R_1$ to $R_3$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl, each $R_4$ is independently alkyl, substituted alkyl, alkenyl, substituted alkenyl, alkynyl, substituted alkynyl, aryl, substituted aryl, cycloalkyl, substituted cycloalkyl, $E_1$ to $E_4$ are each independently —O, —$NR_5$, or —S, wherein $R_5$ is —H or $C_1$-$C_6$ alkyl, and x is 0 to 8.

In still a further embodiment of the invention, there are provided compounds having the structure (IV):

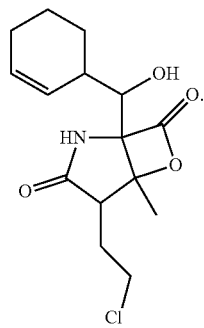

IV

In a further embodiment of the invention, there are provided compounds having the structure (V):

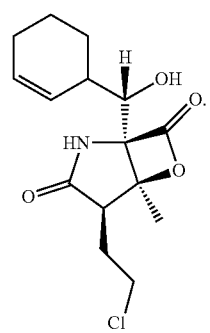

V

In a further embodiment of the invention, there are provided compounds having the structure (VI):

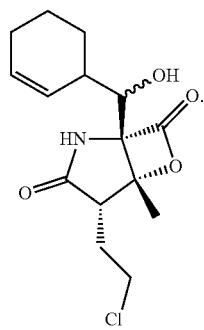

VI

In another embodiment, there are provided pharmaceutical compositions including at least one compound of structures I-VI in a pharmaceutically acceptable carrier therefor.

In another embodiment, there are provided articles of manufacture including packaging material and a pharmaceutical composition contained within the packaging material, wherein the packaging material includes a label which indicates that the pharmaceutical composition can be used for treatment of cell proliferative disorders and wherein the pharmaceutical composition includes at least one compound of structures I-VI.

In yet another embodiment, there are provided methods for treating a mammalian cell proliferative disorder. Such a method can be performed for example, by administering to a subject in need thereof a therapeutically effective amount of a compound having structures I-VI.

In an additional embodiment, there are provided methods for producing a compound of structures I-VI having the ability to inhibit the proliferation of hyperproliferative mammalian cells. Such a method can be performed, for example, by cultivating a culture of a Salinospora sp. strains CNB392 or CNB476 (ATCC # PTA-5275, deposited on Jun. 20, 2003, pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.) and isolating from the culture at least one compound of structure I.

BRIEF DESCRIPTION OF THE DRAWINGS

FIG. 4 compares the cytotoxic activity and dose response curves of Salinosporamide A and Etoposide.

FIG. 15 sets forth the signature nucleotides that strains CNB392 and CNB476 possess within their 16S rDNA, which separate these strains phylogenetically from all other family members of the family Micromonosporaceae.

DETAILED DESCRIPTION OF THE INVENTION

Figure 1:
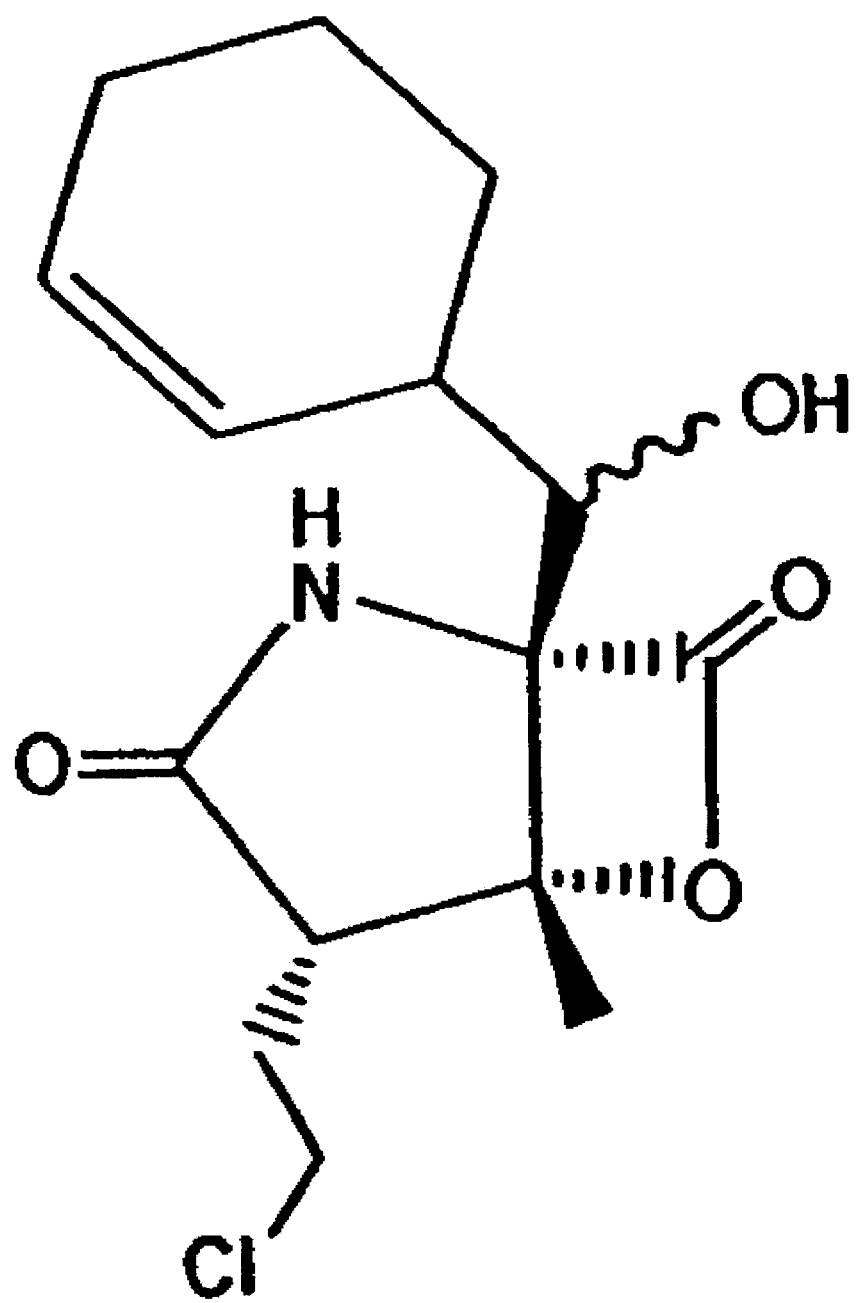
FIG. 1 depicts the chemical structure of an exemplary compound of the invention, Salinosporamide A, with relative stereochemistry.

In one embodiment, there are provided compounds having the structure (I):

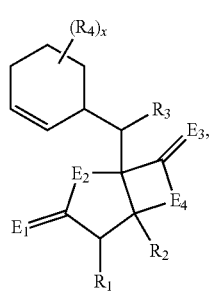

I wherein:
$R_1$ to $R_3$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

Each $R_4$ is independently alkyl, substituted alkyl, alkenyl, substituted alkenyl, alkynyl, substituted alkynyl, aryl, substituted aryl, cycloalkyl, substituted cycloalkyl;

$E_1$ to $E_4$ are each independently —O, —$NR_5$, or —S, wherein $R_5$ is —H or $C_1$-$C_6$ alkyl; and x is 0 to 8.

In a further embodiment of the invention, there are provided compounds having the structure (II):

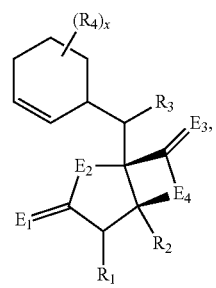

II wherein:
$R_1$ to $R_3$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

Each $R_4$ is independently alkyl, substituted alkyl, alkenyl, substituted alkenyl, alkynyl, substituted alkynyl, aryl, substituted aryl, cycloalkyl, substituted cycloalkyl;

$E_1$ to $E_4$ are each independently —O, —$NR_5$, or —S, wherein $R_5$ is —H or $C_1$-$C_6$ alkyl; and x is 0 to 8.

In one embodiment, there are provided compounds having the structure (III):

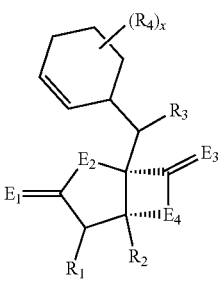

III wherein:
$R_1$ to $R_3$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl, each $R_4$ is independently alkyl, substituted alkyl, alkenyl, substituted alkenyl, alkynyl, substituted alkynyl, aryl, substituted aryl, cycloalkyl, substituted cycloalkyl, $E_1$ to $E_4$ are each independently —O, —$NR_5$, or —S, wherein $R_5$ is —H or $C_1$-$C_6$ alkyl, and x is 0 to 8.

In still a further embodiment of the invention, there are provided compounds having the structure (IV):

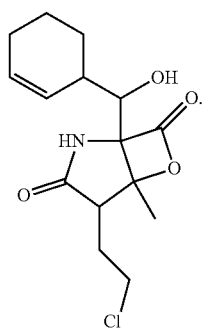

IV

In a further embodiment of the invention, there are provided compounds having the structure (V):

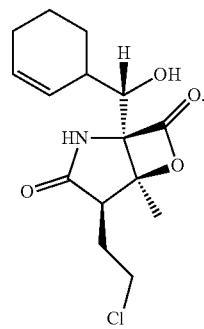

V

In a further embodiment of the invention, there are provided compounds having the structure (VI):

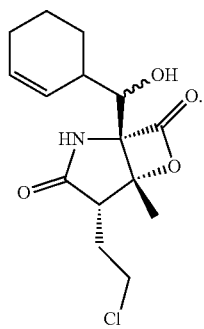

VI

As used herein, the term "alkyl" refers to a monovalent straight or branched chain hydrocarbon group having from one to about 12 carbon atoms, including methyl, ethyl, n-propyl, isopropyl, n-butyl, isobutyl, tert-butyl, n-hexyl, and the like.

As used herein, "substituted alkyl" refers to alkyl groups further bearing one or more substituents selected from hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, —C(O)H, acyl, oxyacyl, carboxyl, sulfonyl, sulfonamide, sulfuryl, and the like.

As used herein, "lower alkyl" refers to alkyl groups having from 1 to about 6 carbon atoms.

As used herein, "alkenyl" refers to straight or branched chain hydrocarbyl groups having one or more carbon-carbon double bonds, and having in the range of about 2 up to 12 carbon atoms, and "substituted alkenyl" refers to alkenyl groups further bearing one or more substituents as set forth above.

As used herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heteroaryl" refers to aromatic rings containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

As used herein, "alkoxy" refers to the moiety —O-alkyl-, wherein alkyl is as defined above, and "substituted alkoxy" refers to alkoxyl groups further bearing one or more substituents as set forth above.

As used herein, "thioalkyl" refers to the moiety —S-alkyl-, wherein alkyl is as defined above, and "substituted thioalkyl" refers to thioalkyl groups further bearing one or more substituents as set forth above.

As used herein, "cycloalkyl" refers to ring-containing alkyl groups containing in the range of about 3 up to 8 carbon atoms, and "substituted cycloalkyl" refers to cycloalkyl groups further bearing one or more substituents as set forth above.

As used herein, "heterocyclic", refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

In certain embodiments, there are provided compounds of structures I-III wherein $E_1$, $E_3$, and $E_4$ are —O, and $E_2$ is —NH.

In certain embodiments, there are provided compounds of structures I-III wherein $R_1$ and $R_2$ are —H, alkyl, or substituted alkyl, and $R_3$ is hydroxy or alkoxy. In some embodiments, $R_1$ is substituted alkyl. Exemplary substituted alkyls contemplated for use include halogenated alkyls, such as for example chlorinated alkyls.

The compounds of the invention may be formulated into pharmaceutical compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, p-toluenesulfonic, methanesulfonic acid, oxalic, tartaric, mandelic, and the like. Salts of the invention include amine salts formed by the protonation of an amino group with inorganic acids such as hydrochloric acid, hydrobromic acid, hydroiodic acid, sulfuric acid, phosphoric acid, and the like. Salts of the invention also include amine salts formed by the protonation of an amino group with suitable organic acids, such as p-toluenesulfonic acid, acetic acid, and the like. Additional excipients which are contemplated for use in the practice of the present invention are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference.

The compounds according to this invention may contain one or more asymmetric carbon atoms and thus occur as racemates and racemic mixtures, single enantiomers, diastereomeric mixtures and individual diastereomers. The term "stereoisomer" refers to chemical compounds which differ from each other only in the way that the different groups in the molecules are oriented in space. Stereoisomers have the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. All such isomeric forms of these compounds are expressly included in the present invention.

Each stereogenic carbon may be of R or S configuration. Although the specific compounds exemplified in this application may be depicted in a particular configuration, compounds having either the opposite stereochemistry at any given chiral center or mixtures thereof are also envisioned. When chiral centers are found in the derivatives of this invention, it is to be understood that this invention encompasses all possible stereoisomers. The terms "optically pure compound" or "optically pure isomer" refers to a single stereoisomer of a chiral compound regardless of the configuration of the compound.

Exemplary invention compounds of structure I are shown below:

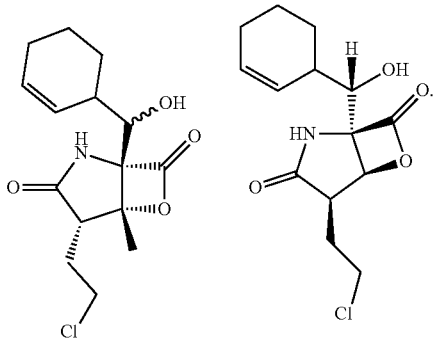 [SMILES: C[C@]12OC(=O)[C@@]1(C(O)C1C=CCCC1)NC(=O)[C@H]2CCCl ; O=C1N[C@@]2([C@@H](O)C3C=CCCC3)C(=O)O[C@H]2[C@H]1CCCl]

Salinosporamide A exhibits a molecular structure having a variety of functional groups (lactone, alkylhalide, amide, hydroxide) that can be chemically modified to produce synthetic derivatives. Accordingly, exemplary invention compound Salinosporamide A provides an excellent lead structure for the development of synthetic and semisynthetic derivatives. Indeed, Salinosporamide A can be derivatized to improve pharmacokinetic and pharmacodynamic properties, which facilitate administration and increase utility of the derivatives as anti-neoplastic agents. Procedures for chemically modifying invention salinosporamide compounds to produce additional compounds within the scope of the present invention are available to those of ordinary skill in the art.

Figure 3:
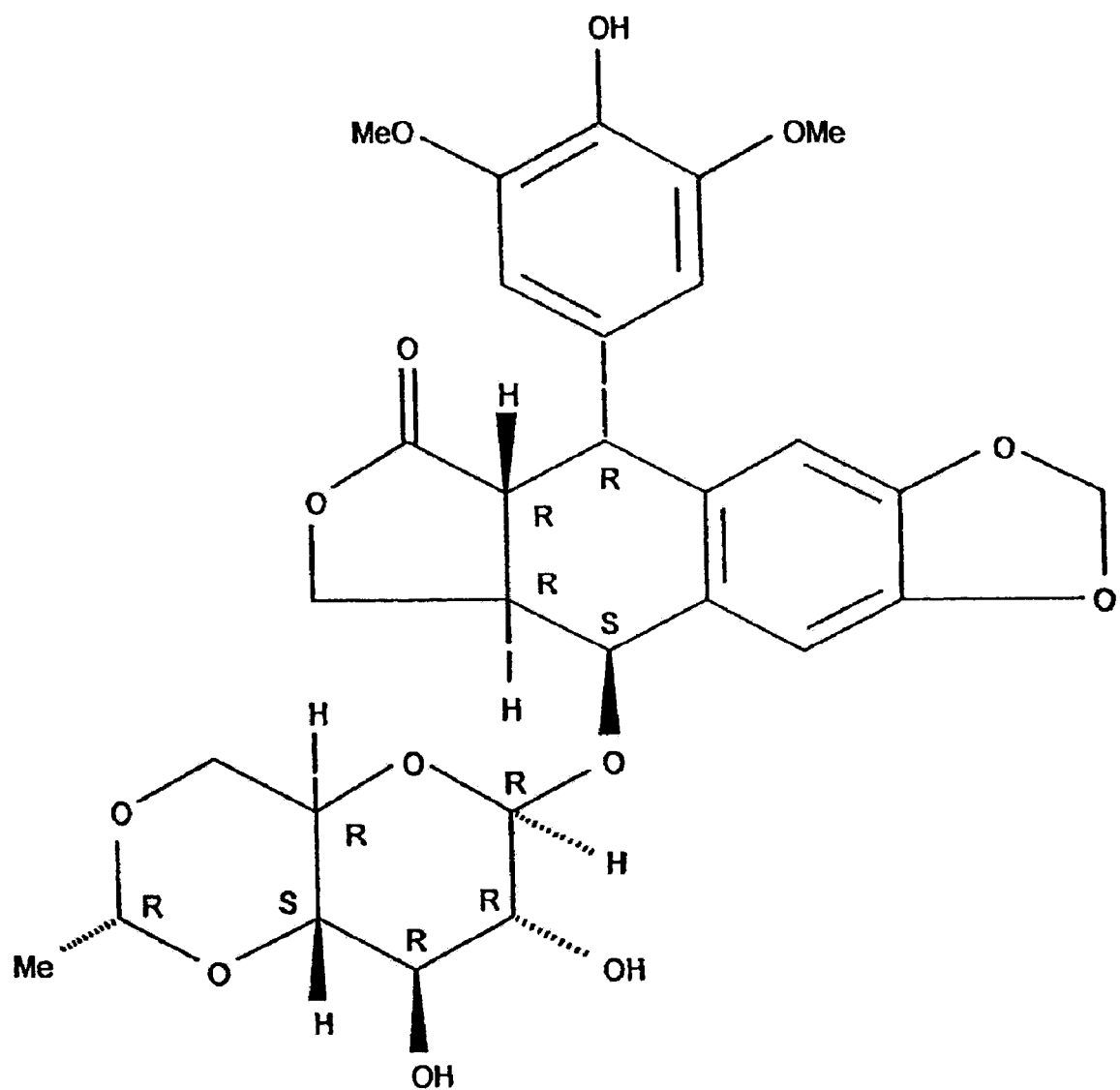
FIG. 3 depicts the chemical structure of Etoposide, an anti-neoplastic agent in therapy against several human cancers.

Salinosporamide A shows strong cytotoxic activity against human colon cancer cells in the HTC-116 cell assays. The $IC_{50}$ of 11 ng/mL exceeds the activity of etoposide (see FIG. 3, $IC_{50}$ 828 ng/mL), an anticancer drug used for treatment of a number of cancers, by almost two orders of magnitude (see FIG. 4). This high activity makes invention salinosporamides excellent candidates for use in the treatment of various human cancers, especially slow growing, refractile cancers for which there are no therapies. Salinosporamide A is specific to inhibition of mammalian cells and shows little anifungal activity against *Candida albicans* ($IC_{50}$ 250 µg/mL) and no antibacterial activity (*Staphylococcus aureus*, *Enterococcus faecium*). The $IC_{50}$ of Salinosporamide A is far lower than the strongest chemotherapeutic agents currently in use or in clinical trials.

Salinosporamide A is a fermentation product of the marine actinomycete strains CNB392 and CNB476. These strains are members of the order Actinomycetales, which are high G+C gram positive bacteria. The novelty of CNB392 and CNB476 is at the genus level. Invention compounds set forth herein are produced by certain "Salinospora" sp. In some embodiments, invention compounds are produced by "Salinospora" sp. strains CNB392 and CNB476. To that end, the CNB476 strains of "Salinospora" sp. were deposited on Jun. 20, 2003, pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No PTA-5275.

As is the case with other organisms, the characteristics of "Salinospora" sp. are subject to variation. For example, recombinants, variants, or mutants of the specified strain may be obtained by treatment with various known physical and chemical mutagens, such as ultraviolet ray, X-rays, gamma rays, and N-methyl-N'-nitro-N-nitrosoguanidine. All natural and induced variants, mutants, and recombinants of the specified strain which retain the characteristic of producing a compound of the invention are intended to be within the scope of the claimed invention.

Figure 5:
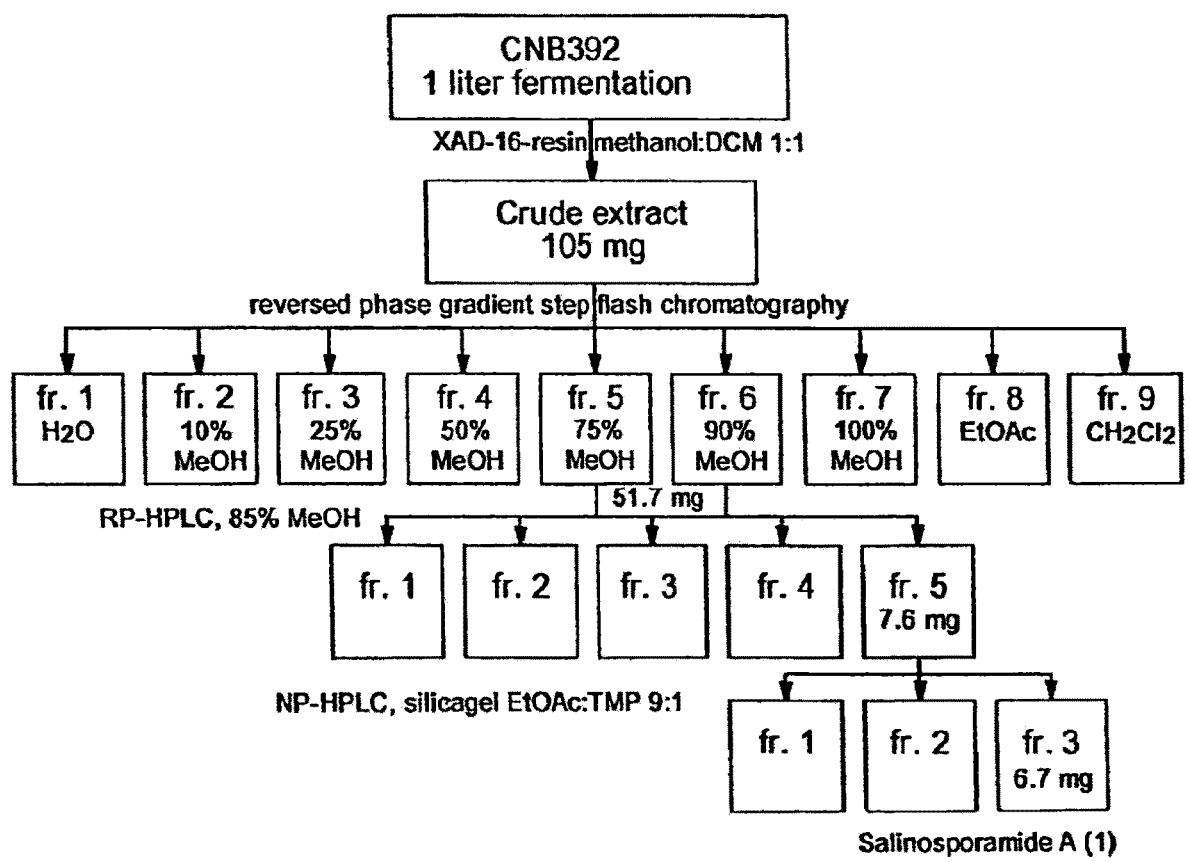
FIG. 5 is a block diagram depicting an exemplary separation scheme used to isolate Salinosporamide A.
Figure 6:
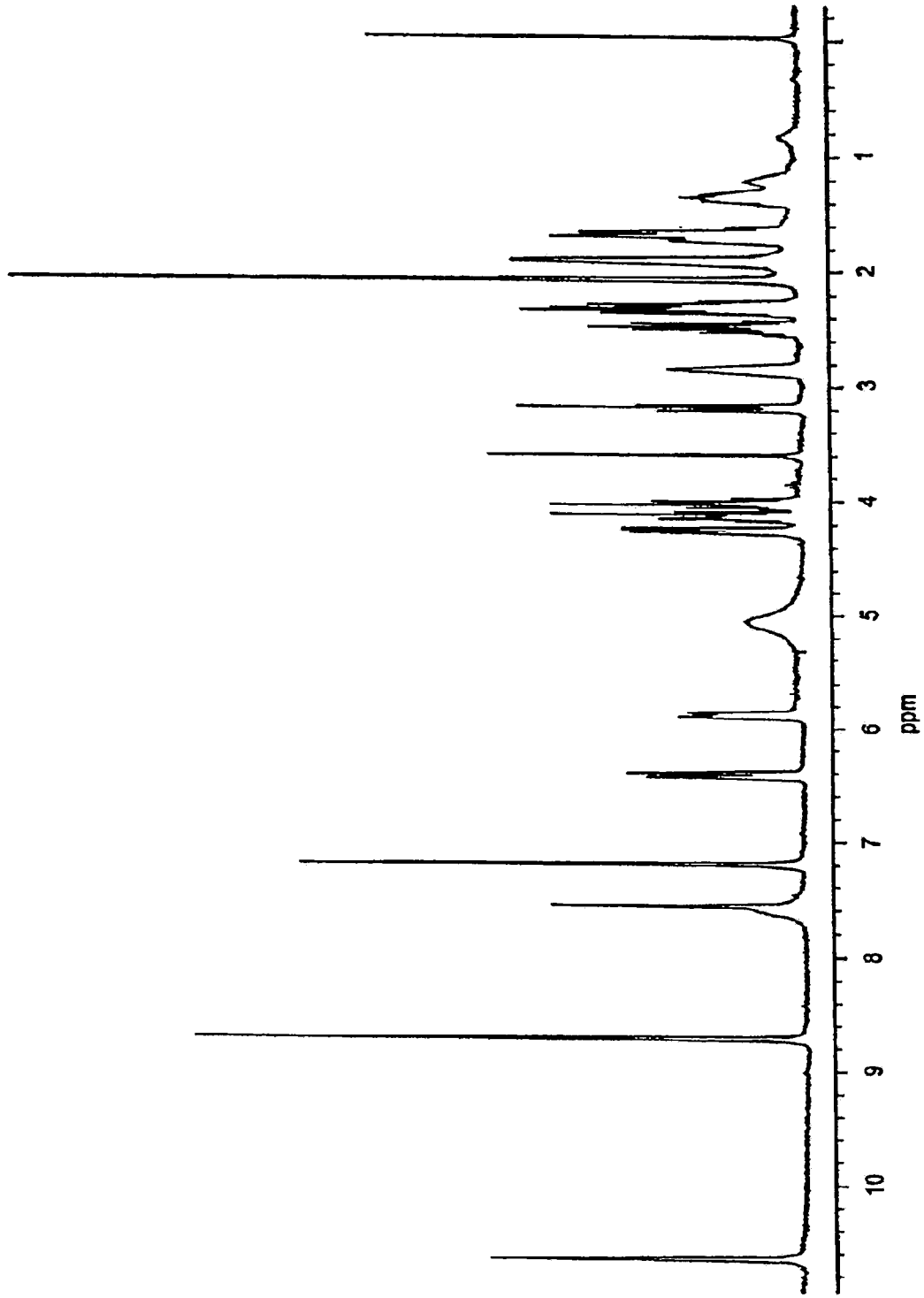
FIGS. 6, 7, 8, 9, 10, 11, 12, 13 and 14 set forth NMR, IR, and UV spectroscopic data used to elucidate the structure of Salinosporamide A.
Figure 7:
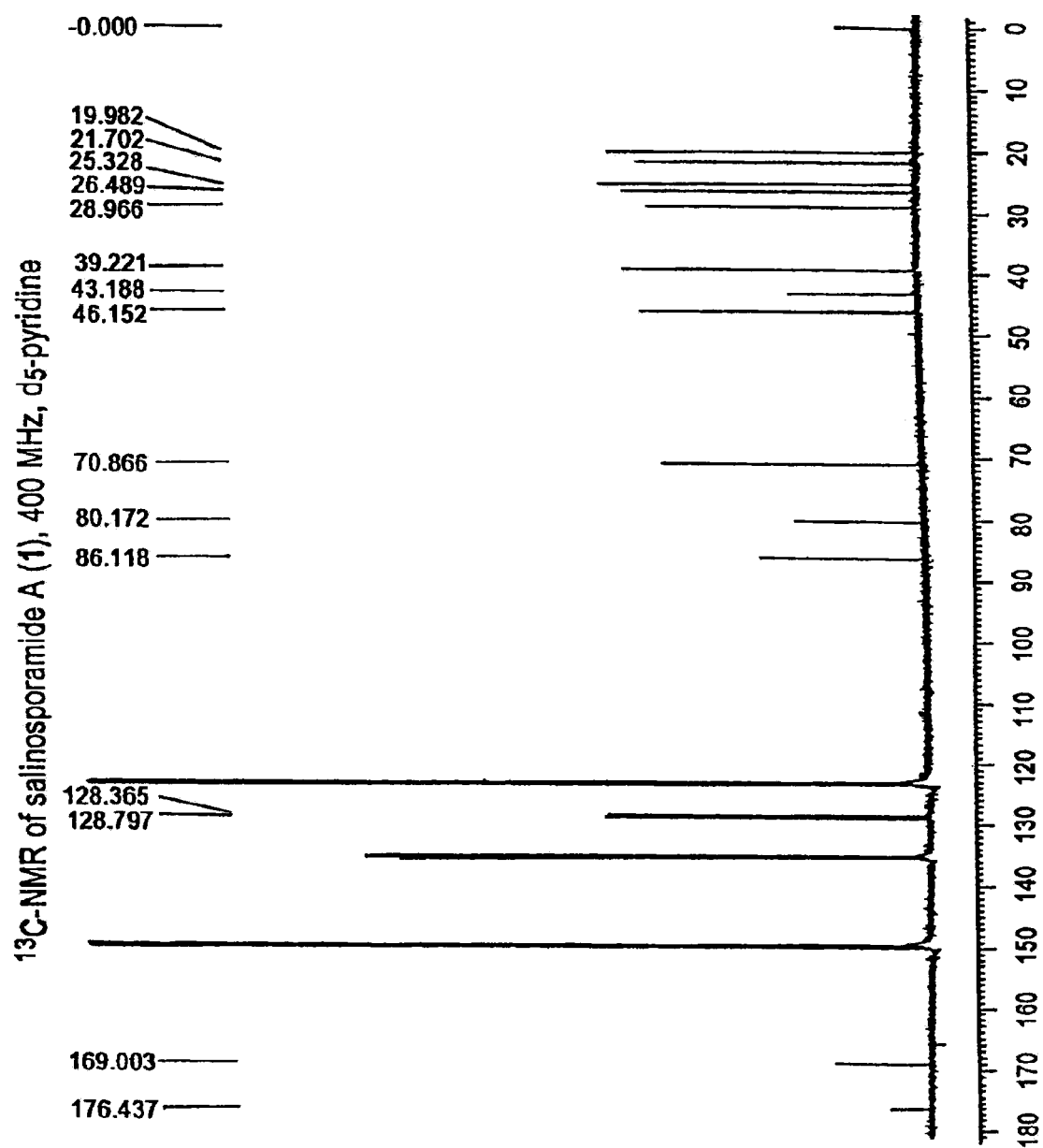
Figure 8:
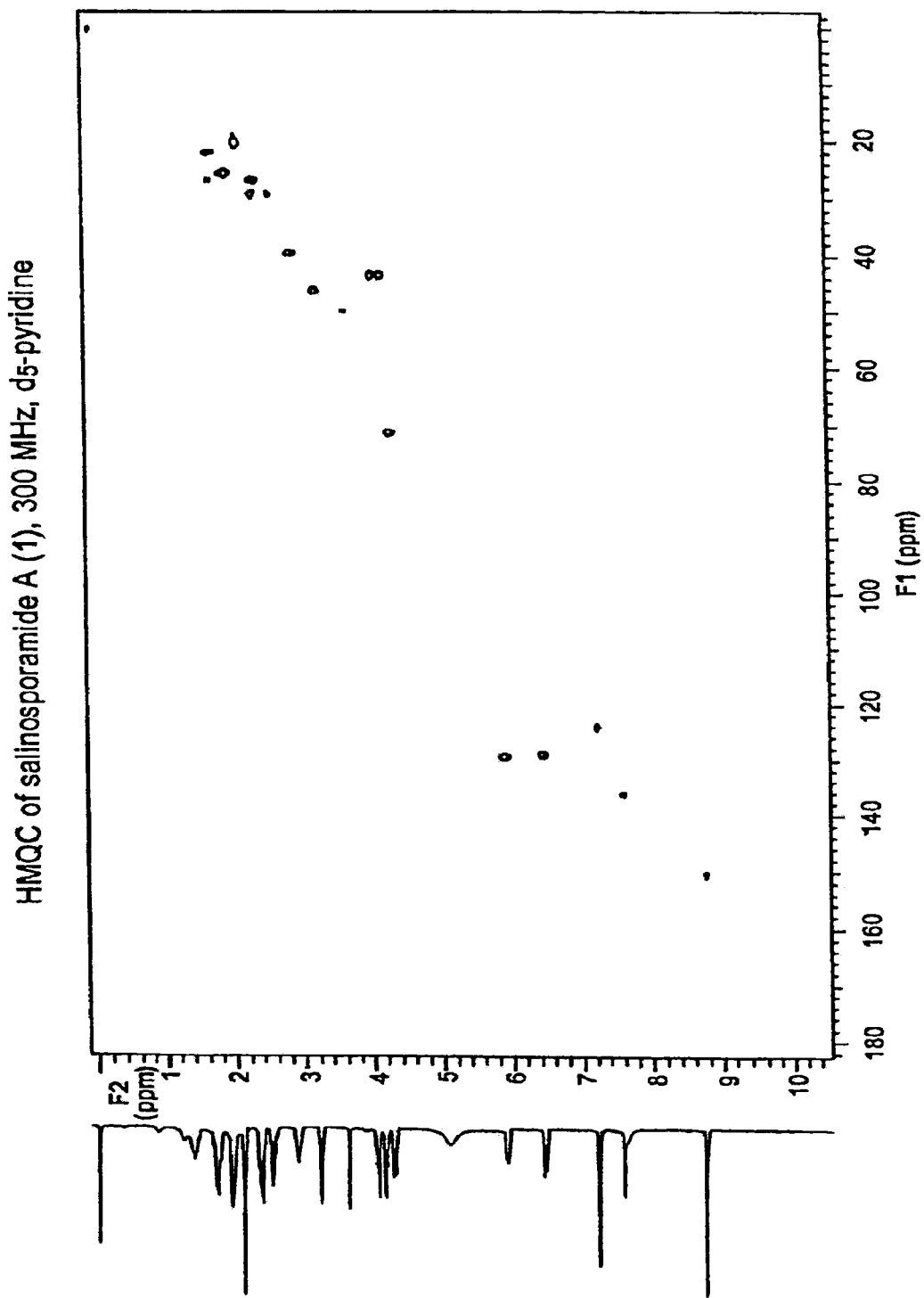
Figure 9:
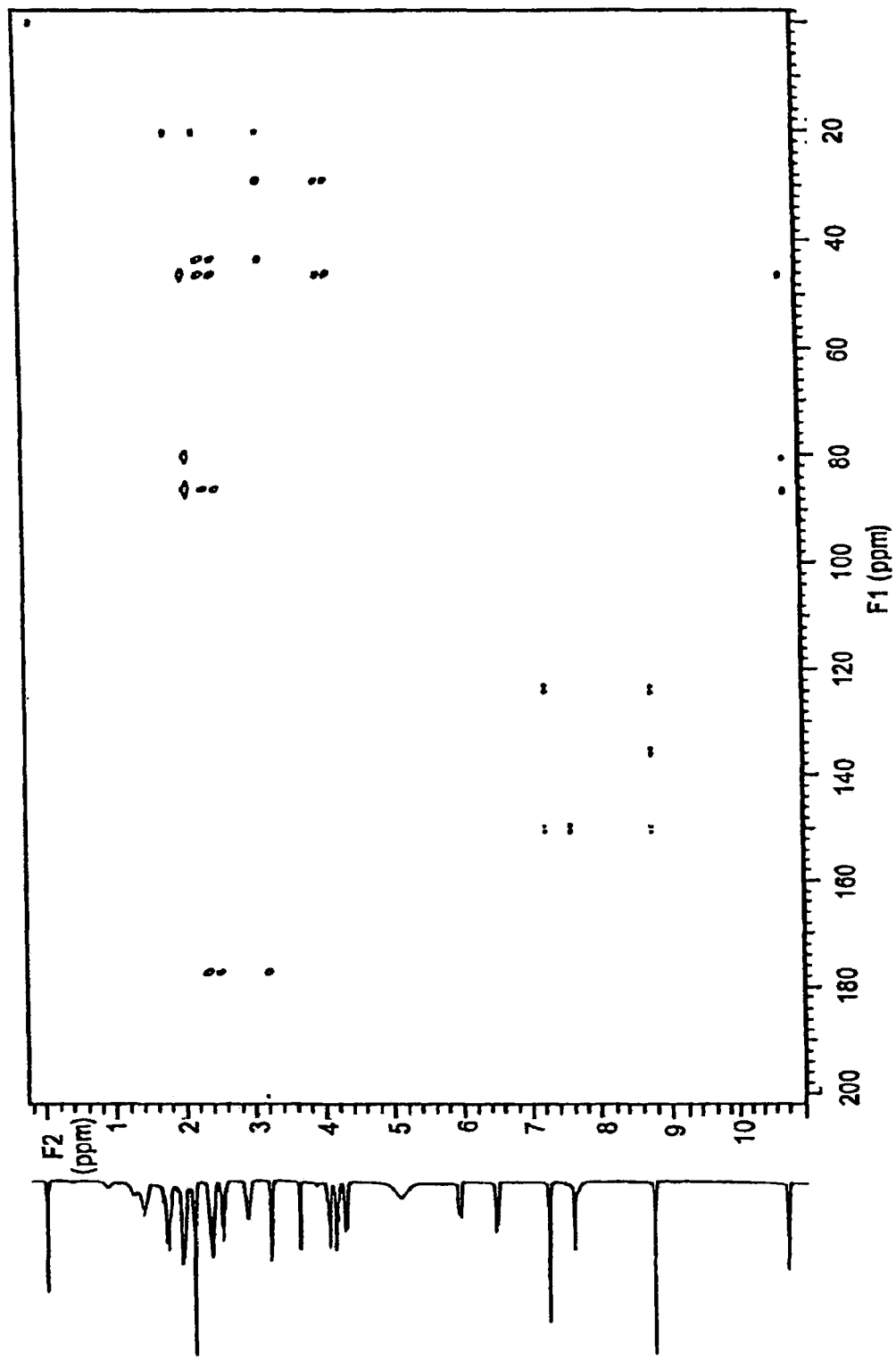
Figure 10:
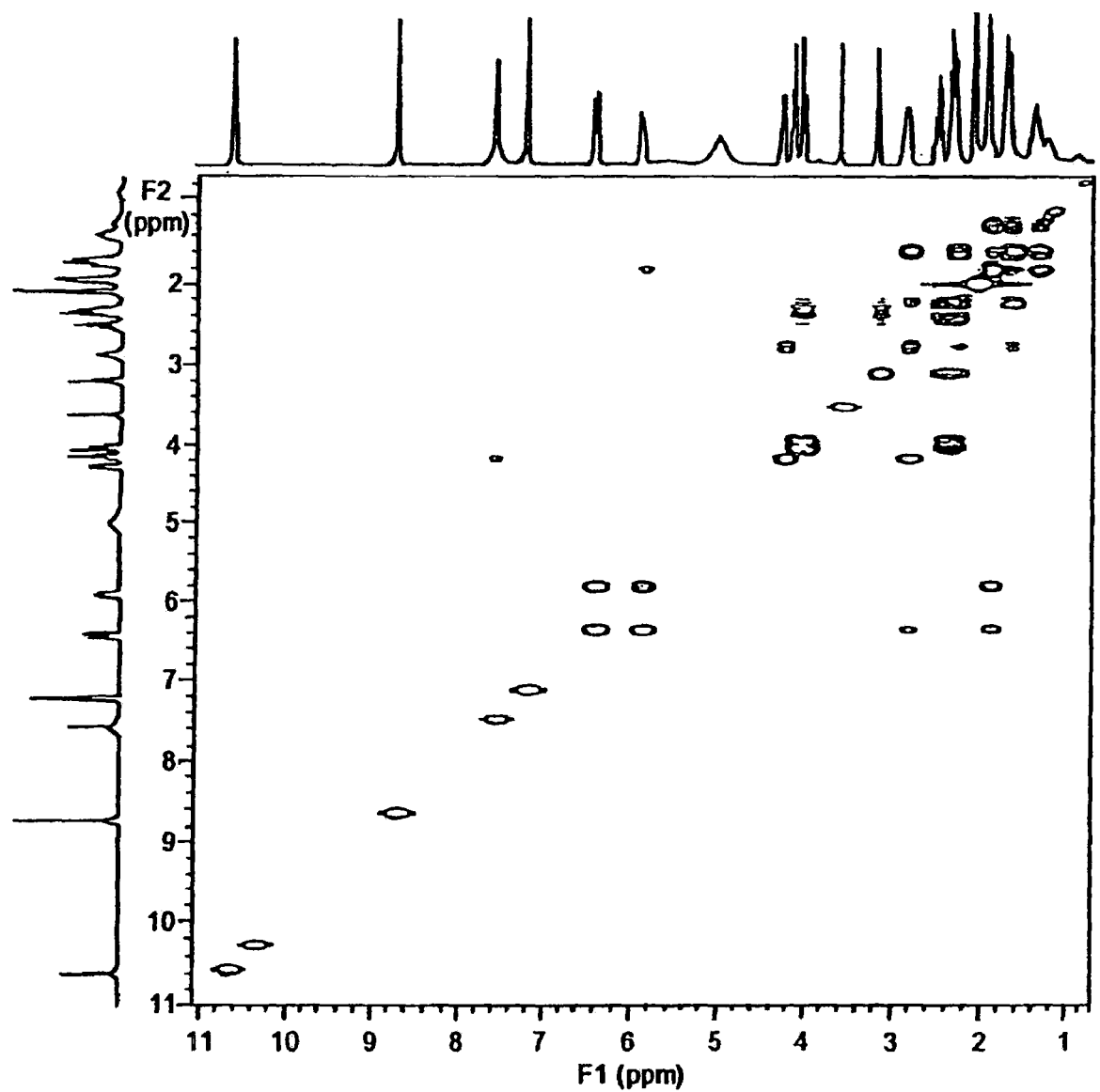
Figure 11:
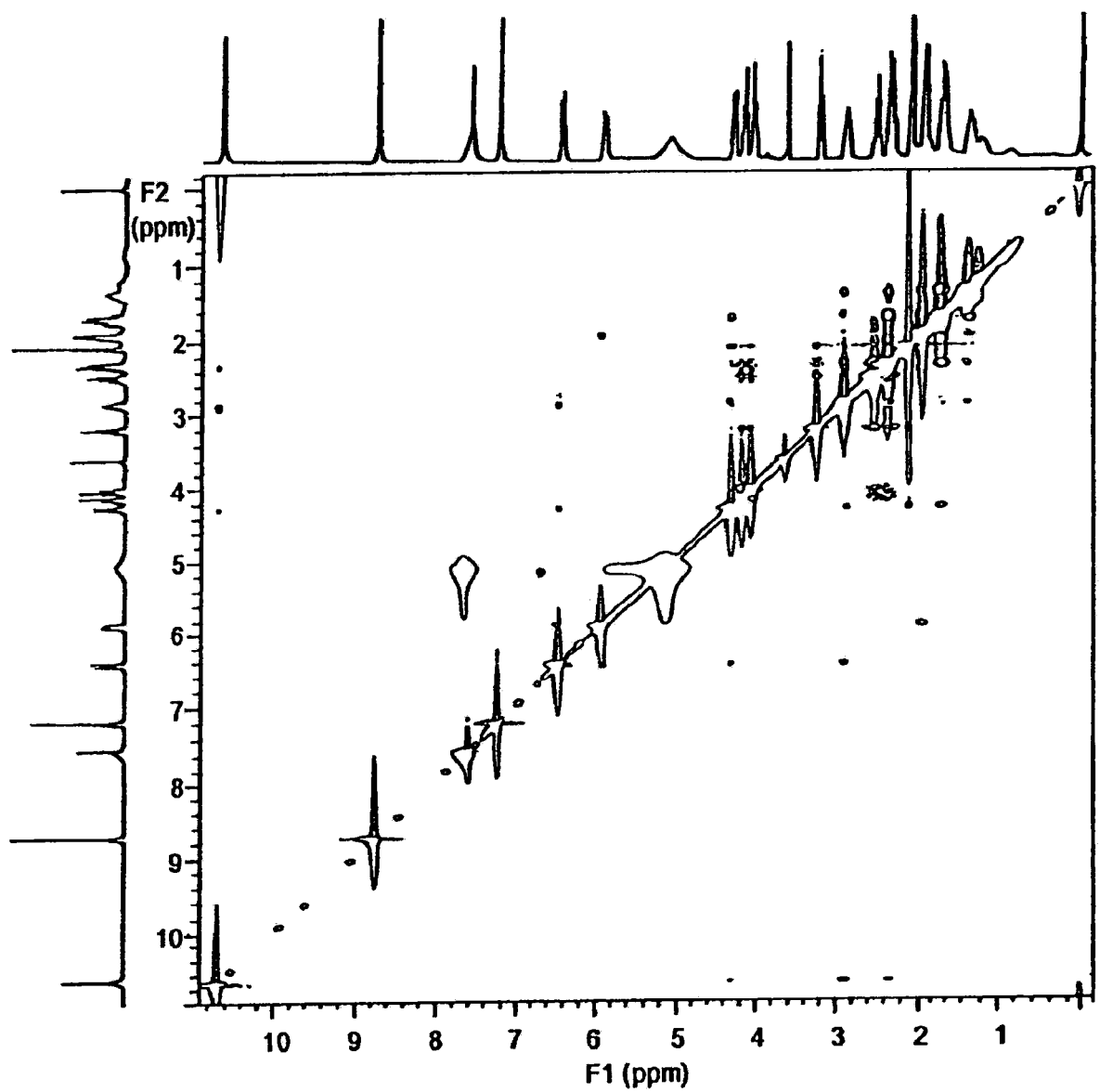
Figure 12:
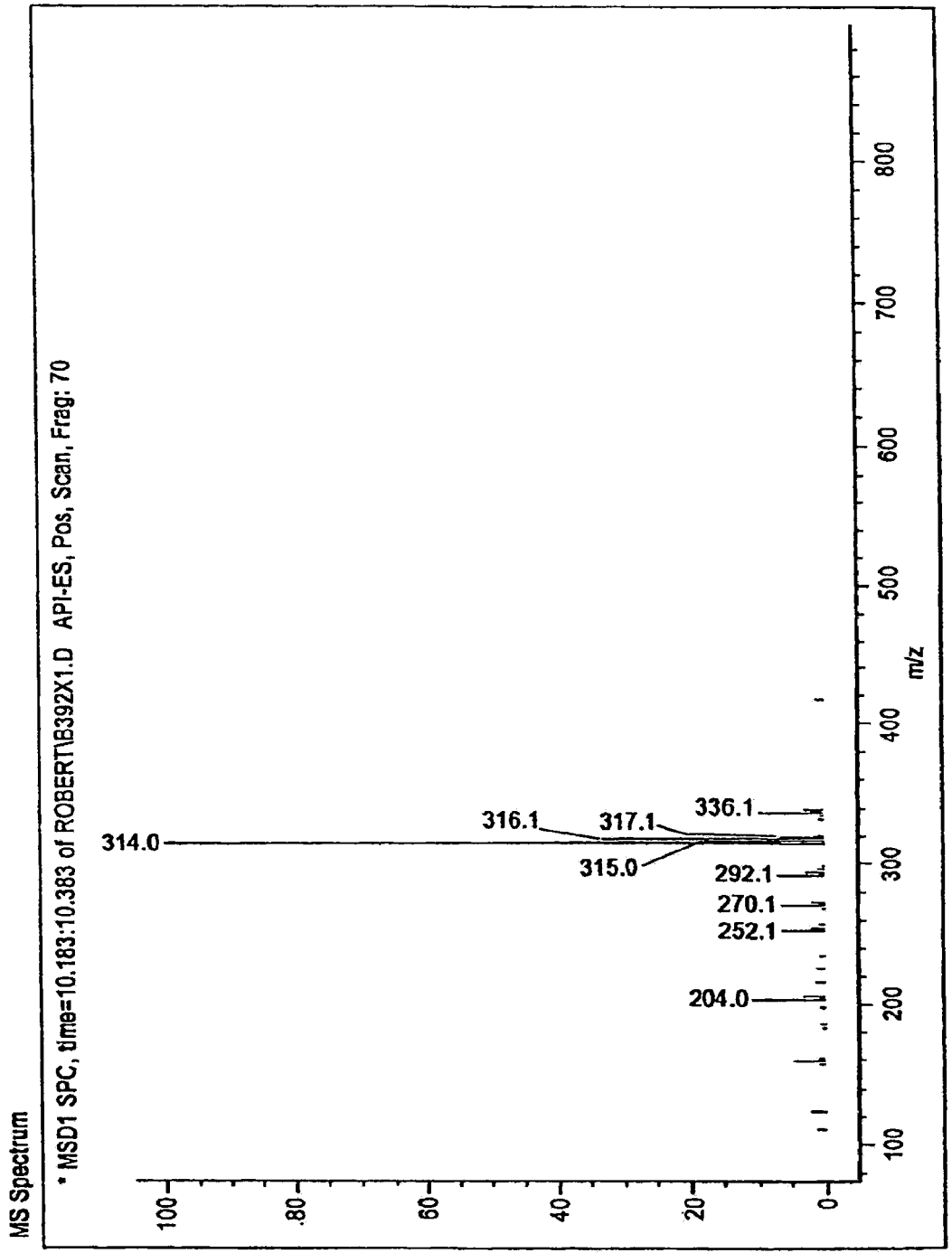
Figure 13:
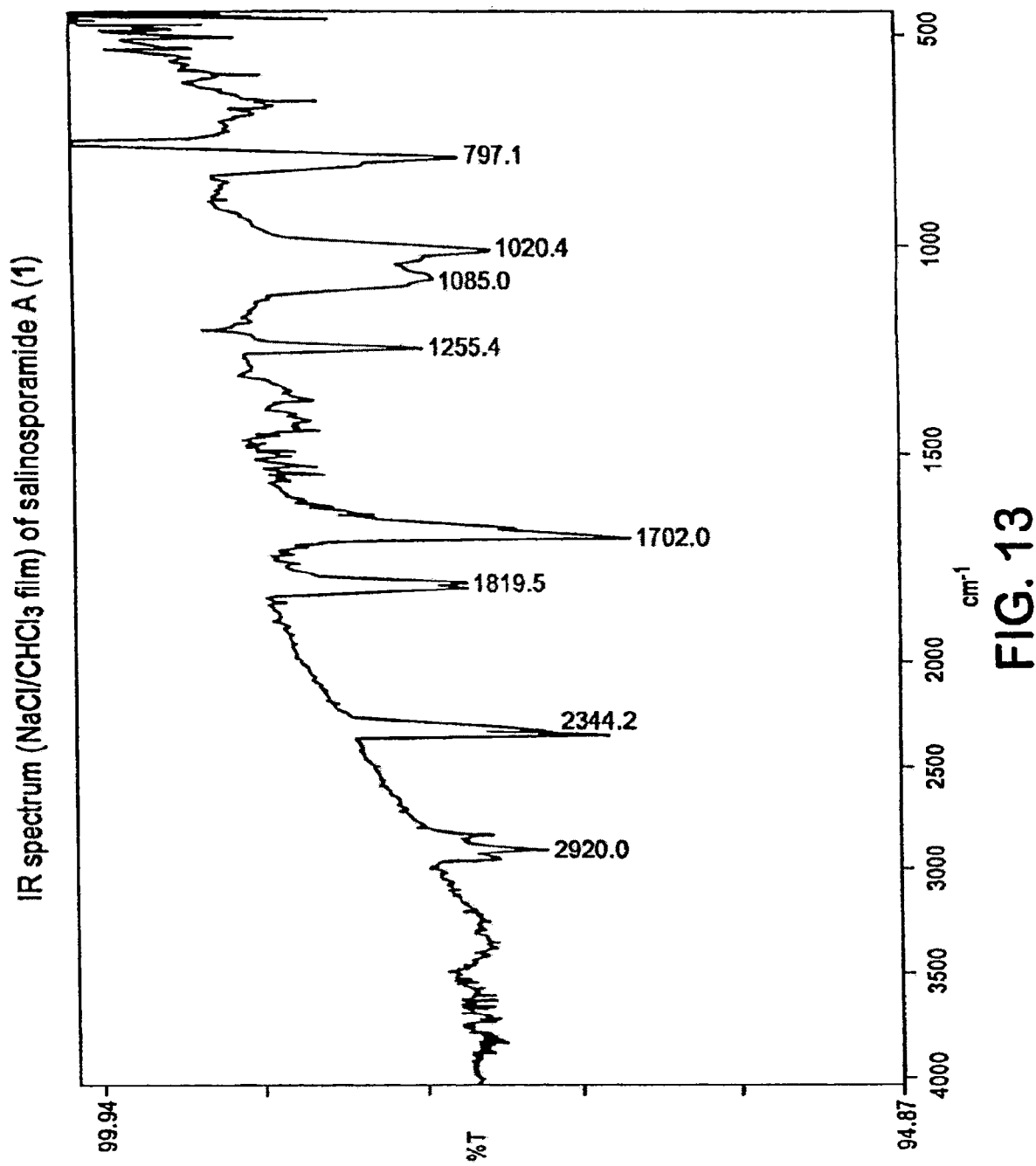
Figure 14:
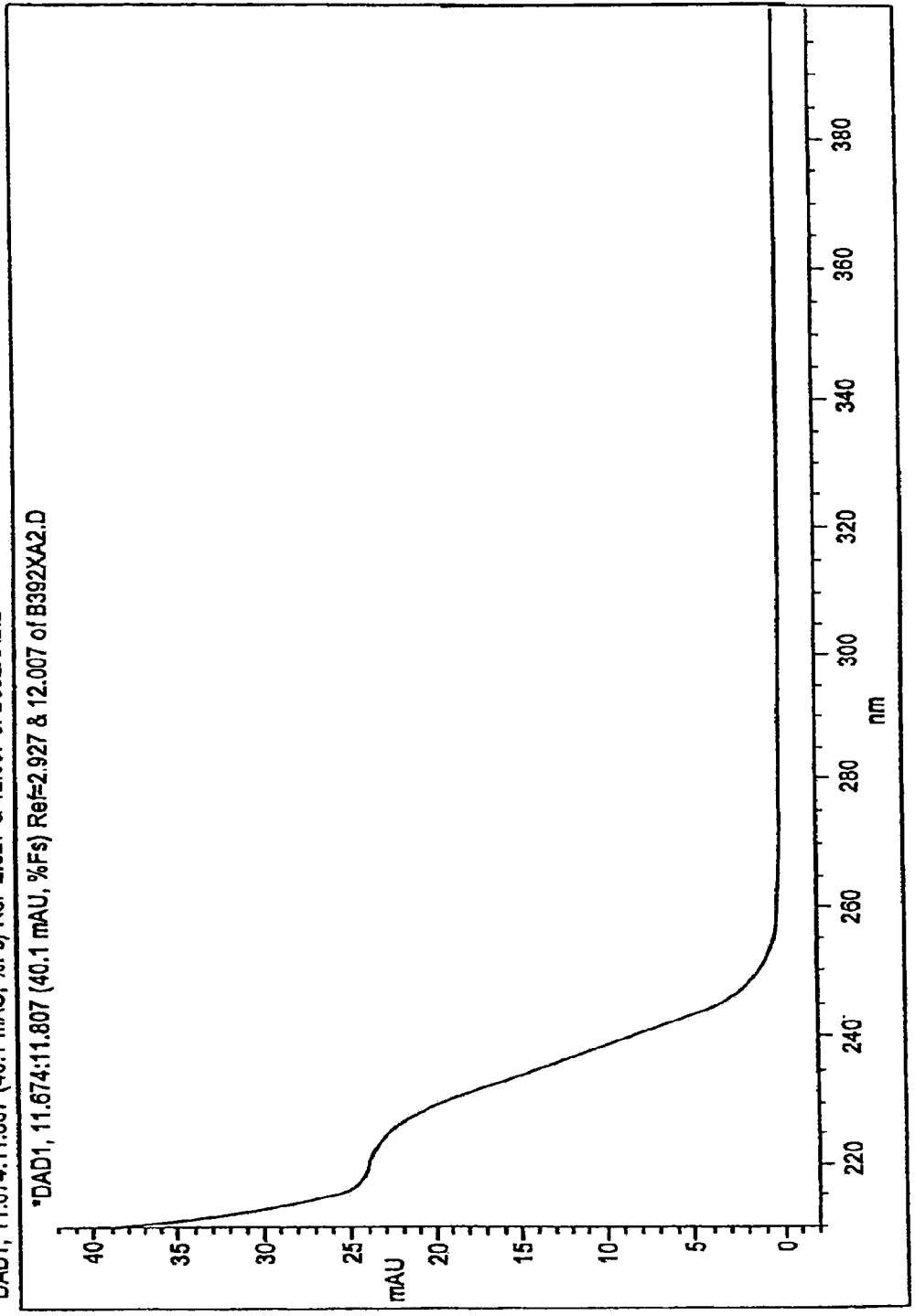

Invention compounds can be prepared, for example, by bacterial fermentation, which generates the compounds in sufficient amounts for pharmaceutical drug development and for clinical trials. In some embodiments, invention compounds are produced by fermentation of the actinomycete strains CNB392 and CNB476 in A1Bfe+C or CKA-liquid media. Essential trace elements which are necessary for the growth and development of the culture should also be included in the culture medium. Such trace elements commonly occur as impurities in other constituents of the medium in amounts sufficient to meet the growth requirements of the organisms. It may be desirable to add small amounts (i.e., 0.2 mL/L) of an antifoam agent such as polypropylene glycol (M.W. about 2000) to large scale cultivation media if foaming becomes a problem. The organic metabolites are isolated by adsorption onto an amberlite XAD-16 resin. For example, Salinosporamide A is isolated by elution of the XAD-16 resin with methanol:

dichlormethane 1:1, which affords about 105 mg crude extract per liter of culture. Salinosporamide A is then isolated from the crude extract by reversed-phase flash chromatography followed by reverse-phase HPLC and normal phase HPLC, which yields 6.7 mg of Salinosporamide A. FIG. 5 sets forth a block diagram outlining isolation and separation protocols for invention compounds.

The structure of Salinosporamide A was elucidated by a variety of NMR techniques, mass spectroscopy, IR, and UV spectroscopy, as set forth in FIGS. 6-14.

The absolute structure of salinosporamide A, and confirmation of the overall structure of salinosporamide A, was achieved by single-crystal X-ray diffraction analysis (see Example 3).

The present invention also provides articles of manufacture including packaging material and a pharmaceutical composition contained within the packaging material, wherein the packaging material comprises a label which indicates that the pharmaceutical composition can be used for treatment of disorders and wherein the pharmaceutical composition includes a compound according to the present invention. Thus, in one aspect, the invention provides a pharmaceutical composition including a compound of the invention, wherein the compound is present in a concentration effective to treat cell proliferative disorders. The concentration can be determined by one of skill in the art according to standard treatment regimen or as determined by an in vivo animal assay, for example.

Pharmaceutical compositions employed as a component of invention articles of manufacture can be used in the form of a solid, a solution, an emulsion, a dispersion, a micelle, a liposome, and the like, wherein the resulting composition contains one or more invention compounds as an active ingredient, in admixture with an organic or inorganic carrier or excipient suitable for enteral or parenteral applications. Compounds employed for use as a component of invention articles of manufacture may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

Invention pharmaceutical compositions may be administered by any suitable means, for example, orally, such as in the form of tablets, capsules, granules or powders; sublingually; buccally; parenterally, such as by subcutaneous, intravenous, intramuscular, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. Invention compounds may, for example, be administered in a form suitable for immediate release or extended release. Immediate release or extended release may be achieved by the use of suitable pharmaceutical compositions comprising invention compounds, or, particularly in the case of extended release, by the use of devices such as subcutaneous implants or osmotic pumps. Invention compounds may also be administered liposomally.

The invention further provides methods for using invention salinosporamide compounds of structures (I)-(VI) to inhibit the proliferation of mammalian cells by contacting these cells with an invention salinosporamide compound in an amount sufficient to inhibit the proliferation of the mammalian cell. One embodiment is a method to inhibit the proliferation of hyperproliferative mammalian cells. For purposes of this invention, "hyperproliferative mammalian cells" are mammalian cells which are not subject to the characteristic limitations of growth, e.g., programmed cell death (apoptosis). A further preferred embodiment is when the mammalian cell is human. The invention further provides contacting the mammalian cell with at least one invention salinosporamide compound and at least one additional anti-neoplastic agent.

In another embodiment, there are provided methods for treating a mammalian cell proliferative disorder, comprising administering to a subject in need thereof a therapeutically effective amount of a compound of structures (I)-(VI). Cell proliferative disorders that can be effectively treated by the methods of the invention include disorders characterized by the formation of neoplasms. As such, invention compounds are anti-neoplastic agents. As used herein, "neoplastic" pertains to a neoplasm, which is an abnormal growth, such growth occurring because of a proliferation of cells not subject to the usual limitations of growth. As used herein, "anti-neoplastic agent" is any compound, composition, admixture, co-mixture or blend which inhibits, eliminates, retards or reverses the neoplastic phenotype of a cell. In certain embodiments, the neoplasms are selected from mammory, small-cell lung, non-small-cell lung, colorectal, leukemia, melanoma, pancreatic adenocarcinoma, central nervous system (CNS), ovarian, prostate, sarcoma of soft tissue or bone, head and neck, gastric which includes thyroid and non-Hodgkin's disease, stomach, myeloma, bladder, renal, neuroendocrine which includes thyroid and non-Hodgkin's disease and Hodgkin's disease neoplasms. In one embodiment, the neoplasms are colorectal.

Chemotherapy, surgery, radiation therapy, therapy with biologic response modifiers, and immunotherapy are currently used in the treatment of cancer. Each mode of therapy has specific indications which are known to those of ordinary skill in the art, and one or all may be employed in an attempt to achieve total destruction of neoplastic cells. Chemotherapy utilizing one or more invention salinosporamide compounds is provided by the present invention. Moreover, combination chemotherapy, chemotherapy utilizing invention salinosporamide compounds in combination with other neoplastic agents, is also provided by the invention as combination therapy is generally more effective than the use of single anti-neoplastic agents. Thus, a further aspect of the present invention provides compositions containing a therapeutically effective amount of at least one invention salinosporamide compound in combination with at least one other anti-neoplastic agent. Such compositions can also be provided together with physiologically tolerable liquid, gel or solid carriers, diluents, adjuvants and excipients. Such carriers, diluents, adjuvants and excipients may be found in the United States Pharmacopeia Vol. XXII and National Formulary Vol XVII, U.S. Pharmacopeia Convention, Inc., Rockville, Md. (1989), the contents of which are herein incorporated by reference. Additional modes of treatment are provided in AHFS Drug Information, 1993 ed. by the American Hospital Formulary Service, pp. 522-660, the contents of which are herein incorporated by reference.

Anti-neoplastic agents which may be utilized in combination with an invention salinosporamide compound include those provided in The Merck Index, 11th ed. Merck & Co., Inc. (1989) pp. Ther 16-17, the contents of which are hereby incorporated by reference. In a further embodiment of the invention, anti-neoplastic agents may be antimetabolites which may include, but are not limited to, methotrexate, 5-fluorouracil, 6-mercaptopurine, cytosine arabinoside, hydroxyurea, and 2-chlorodeoxyadenosine. In another embodiment of the present invention, the anti-neoplastic agents contemplated are alkylating agents which may include, but are not limited to, cyclophosphamide, melphalan, busulfan, paraplatin, chlorambucil, and nitrogen mustard. In a further embodiment of the invention, the antineoplastic agents are plant alkaloids which may include, but are not limited to, vincristine, vinblastine, taxol, and etoposide. In a further embodiment of the invention, the anti-neoplastic agents contemplated are antibiotics which may include, but are not limited to, doxorubicin (adriamycin), daunorubicin, mitomycin c, and bleomycin. In a further embodiment of the invention, the anti-neoplastic agents contemplated are hormones which may include, but are not limited to, calusterone, diomostavolone, propionate, epitiostanol, mepitiostane, testolactone, tamoxifen, polyestradiol phosphate, megesterol acetate, flutamide, nilutamide, and trilotane. In a further embodiment of the invention, the anti-neoplastic agents contemplated include enzymes which may include, but are not limited to, L-Asparaginase or aminoacridine derivatives which may include, but are not limited to, amsacrine. Additional anti-neoplastic agents include those provided in Skeel, Roland T., "Antineoplastic Drugs and Biologic Response Modifier: Classification, Use and Toxicity of Clinically Useful Agents," Handbook of Cancer Chemotherapy (3rd ed.), Little Brown & Co. (1991), the contents of which are herein incorporated by reference.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated.

The term "therapeutically effective amount" means the amount of the subject compound that will elicit the biological or medical response of a tissue, system, animal or human that is being sought by the researcher, veterinarian, medical doctor or other clinician, e.g., lessening of the effects/symptoms of cell proliferative disorders.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment. Administration of the invention compounds can be prior to, simultaneously with, or after administration of another therapeutic agent or other anti-neoplastic agent.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed.

Compounds and compositions of the invention can be administered to mammals for veterinary use, such as for domestic animals, and clinical use in humans in a manner similar to other therapeutic agents. In general, the dosage required for therapeutic efficacy will vary according to the type of use and mode of administration, as well as the particularized requirements of individual hosts. Ordinarily, dosages will range from about 0.001 to 1000 μg/kg, more usually 0.01 to 10 μg/kg, of the host body weight. Alternatively, dosages within these ranges can be administered by constant infusion over an extended period of time, usually exceeding 24 hours, until the desired therapeutic benefits have been obtained. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The invention will now be described in greater detail by reference to the following non-limiting examples.

EXAMPLES

Methods and Materials

HPLC-Purification of invention compounds was accomplished by RP-MPLC on $C_{18}$-solid phase (Aldrich) using a step gradient on Kontes Flex-columns (15×7 mm). Semi-preparative HPLC was performed on an isocratic HPLC system with a Waters pump 6000H on normal phase column Si-Dynamas-60 Å (250×5 mm) or reversed phase column C18-Dynamax-60 Å, flow 2 mL/minute, with a differential refractomeric detector Waters R401.

LC-MS-The LC-MS chromatography was performed on a Hewlett-Packard system series HP1100 with DAD and MSD1100 detection. The separation was accomplished on reversed phase C18 (Agilent Hypersil ODS 5 μm, column dimension 4.6×100 mm), flow rate 0.7 mL/minute using a standard gradient: 10% acetonitrile, 15 minutes; 98% acetonitrile (Burdick & Jackson high purity solvents). The MS-detection was in ESI positive mode, capillary voltage 3500 eV, fragmentation voltage 70 eV, mass range m/z 100-1000. The APCI-mode was measured at a flow rate of 0.5 mL/minute, positive detection, capillary voltage 3000 eV, fragmentation voltage 70 eV.

NMR-NMR spectra were measured on a Varian 300 MHz gradient field spectrometer with inverse-mode for $^1H$ or 2D-NMR spectra. The 13C and DEPT spectra were measured on a Varian 400 MHz, broad band instrument. The reference is set on the internal standard tetramethylsilane (TMS, 0.00 ppm).

MS-EI-Low resolution MS-EI spectra were performed on a Hewlett-Packard mass spectrometer with magnetic sector field device, heating rate 20° C./minute up to 320° C., direct injection inlet.

FTMS-MALDI-High resolution MS data were obtained by MALDI operating mode on an IonSpec Ultima FT Mass Spectrometer.

IR-Infrared spectra were measured on a Perkin-Elmer FT infrared spectrophotometer using NaCl windows.

Example 1

Isolation and Characterization of "Salinsospora" Species, Culture Nos. CNB392 and CNB476

Figure 2:
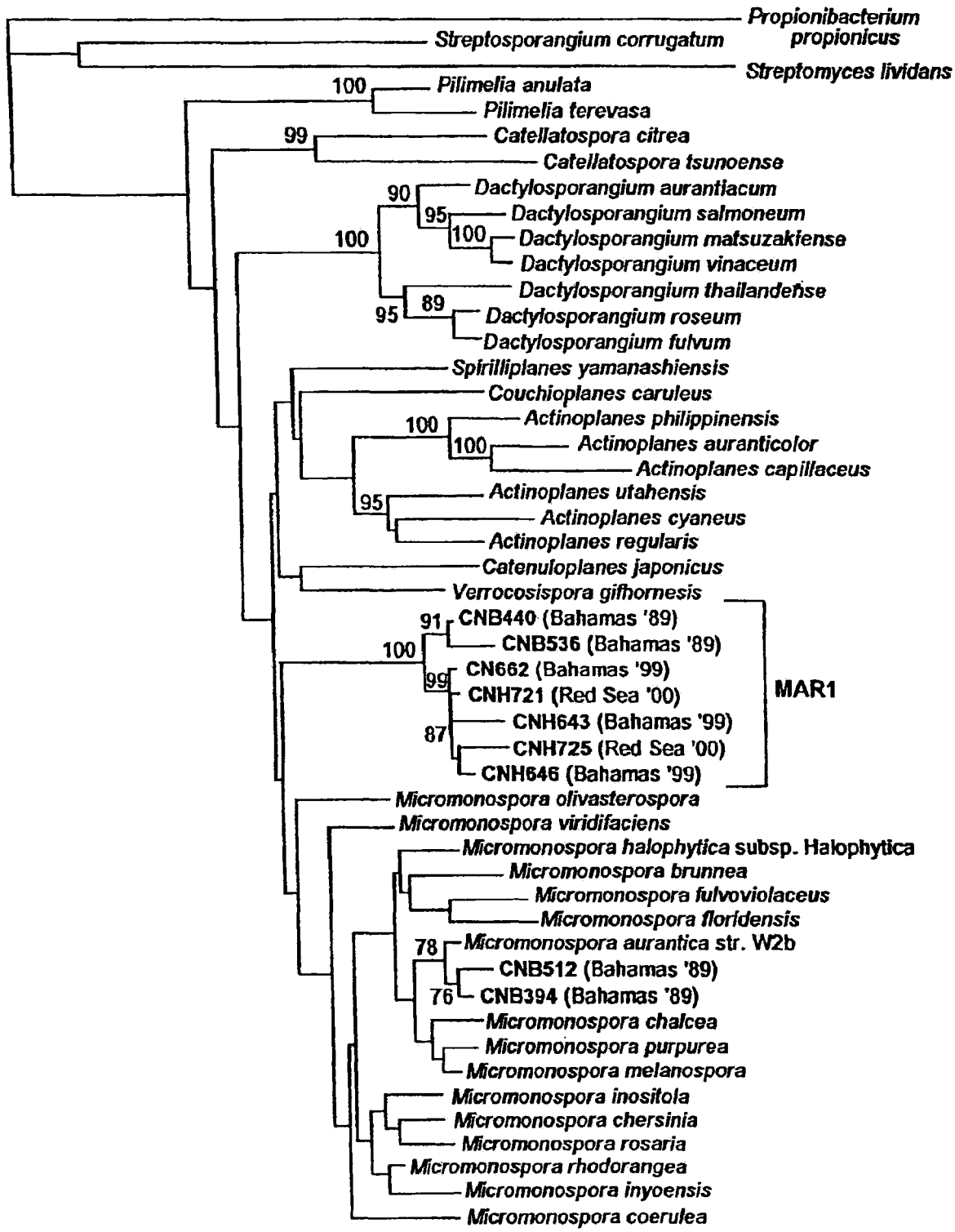
FIG. 2 depicts a phylogenetic tree illustrating the phylogeny of "Salinospora".

CNB392 and CNB476 possess signature nucleotides within their 16S rDNA which separate these strains phylogenetically from all other members of the family Micromonosporaceae (see FIG. 15) These signature nucleotides have been determined to be a definitive marker for members of this group which also have a physiological growth requirement of sodium. Signature nucleotides were aligned to *E. coli* positions 27-1492 using all existing members of the Micromonosporaceae in the Ribosomal Database Project as of 1-31-01. For the "Salinospora" clade, 45 partially sequenced morphotypes displayed all the signature nucleotides from positions 207-468. The seven "Salinospora" isolates sequenced almost in their entirety (see FIG. 2) displayed all of the signatures in FIG. 15.

The strains CNB392 and CNB476 form bright orange to black colonies on agar and lacks aerial mycelia. Dark brown and bright orange diffusible pigments are produced depending upon cellular growth stage. Spores blacken the colony surface and are borne on substrate mycelia. Vegetative mycelia are finely branched and do not fragment. Spores are produced singly or in clusters. Neither sporangia nor spore motility has been observed for these strains. CNB392 and CNB476 have an obligate growth requirement for sodium and will not grow on typical media used for maintenance of other generic members of the Micromonosporaceae. CNB392 and CNB476 have been found to grow optimally on solid media TCG or M1 at 30° C.

| TCG | 3 grams tryptone | M1 | 10 grams starch |
| --- | --- | --- | --- |
|  | 5 grams casitone |  | 4 grams yeast extract |
|  | 4 grams glucose |  | 2 grams peptone |
|  | 18 grams agar (optional) |  | 18 grams agar (optional) |
|  | 1 liter filtered seawater |  | 1 liter filtered seawater |

Fermentation

CNB392 and CNB476 are cultured in shaken A1Bfe+C or CKA-liquid media, 1 liter at 35° C. for 9 days. After 4 days 20 grams Amberlite XAD-16 resin (Sigma, nonionic polymeric adsorbent) is added.

| A1Bfe + C | 10 grams starch | CKA | 5 grams starch |
| --- | --- | --- | --- |
|  | 4 grams yeast extract |  | 4 mL hydrosolubles (50%) |
|  | 2 grams peptone |  | 2 grams menhaden meal |
|  | 1 gram $CaCO_3$ |  | 2 grams kelp powder |
|  | 5 mL KBr (aqueous solution, 20 grams/liter) |  | 2 grams chitosan |
|  | 5 mL $Fe_2(SO_4)_3 \times 4 H_2O$ (8 grams/liter) |  | 1 liter filtered seawater |
|  | 1 liter filtered seawater |  |  |

Extraction

The XAD-16 resin is filtered and the organic extract is eluted with 1 liter ethylacetate followed by 1 liter methanol. The filtrate is then extracted with ethylacetate (3×200 mL). The crude extract from the XAD adsorption is 105 mg. Cytotoxicity on the human colon cancer cell HCT-116 assay is IC50<0.076 µg/mL.

Isolation of Salinosporamide A from CNB392

The crude extract was flash-chromatographed over C18 reversed phase (RP) using a step gradient (FIG. 5). The HCT-116 assay resulted in two active fractions, CNB392-5 and CNB392-6. The combined active fractions (51.7 mg), HCT-116<0.076 µg/mL) were then chromatographed on an isocratic RP-HPLC, using 85% methanol at 2 mL/minute flow as eluent and using refractive index detection. The active fraction CNB392-5/6 (7.6 mg, HCT-116<0.076 µg/mL) was purified on an isocratic normal phase HPLC on silica gel with ethyl acetate:isooctane (9:1) at 2 mL/minute. Salinosporamide A (FIG. 1) was isolated as a colorless, amorphous solid in 6.7 mg per 1 liter yield (6.4%). TLC on silica gel (dichloromethane:methanol 9:1) shows Salinosporamide A at $r_f$=0.6, no UV extinction or fluorescence at 256 nm, yellow with $H_2SO_4$/ethanol, dark red-brown with Godin reagent (vanillin/$H_2SO_4$/$HClO_4$). Salinosporamide A is soluble in $CHCl_3$, methanol, and other polar solvents like DMSO, acetone, acetonitrile, benzene, pyridine, N,N-dimethyformamide, and the like. $^1$HNMR: ($d_5$-pyridine, 300 MHz) 1.37/1.66 (2H, m, $CH_2$), $^3J$=70.2.29 (2H, m, $CH_2$), 1.91 (2H, broad, $CH_2$), 2.07 (3H, s, $CH_3$), 2.32/2.48 (2H, ddd, $^3J$=7.0 Hz, $CH_2$), 2.85 (1H, broad, m, CH), 3.17 (1H, dd, $^3J$=10 Hz, CH), 4.01/4.13 (2H, m, $CH_2$), 4.25 (1H, d, $^3J$=9.0 Hz, CH), 4.98 (1H, broad, OH), 5.88, (1H, ddd, $^3J$=10 Hz, CH), 6.41 (1H, broad d, $^3J$=10 Hz, CH) 10.62 (1H, s, NH).

13C NMR/DEPT: ($d_5$-pyridine, 400 MHz) 176.4 (COOR), 169.0 (CONH), 128.8 (=CH), 128.4 (=CH), 86.1 ($C_q$), 80.2 ($C_q$), 70.9 (CH), 46.2 (CH), 43.2 ($CH_2$), 39.2 (CH), 29.0 ($CH_2$), 26.5 ($CH_2$), 25.3 ($CH_2$), 21.7 ($CH_2$), 20.0 ($CH_3$).

LC-MS (ESI) $t_r$=10.0 minutes, flow 0.7 mL/minute m/z: $(M+H)^+$ 314, $(M+Na)^+$ 336; fragments: $(M+H-CO_2)^+$ 292, $(M+H-CO_2-H_2O)^+$ 270, 252, 204. Cl pattern: $(M+H, 100\%)^+$ 314, $(M+H, 30\%)^+$ 316.

LC MS (APCI): $t_r$=11.7 minutes, flow 0.5 mL/minute m/z: $(M+H)^+$ 314, fragments: $(M+H-CO_2-H_2O)^+$ 270, 252, 232, 216, 160. Cl pattern: $(M+H, 100\%)^+$ 314, $(M+H, 30\%)^+$ 316.

EI: m/z: 269, 251, 235, 217, 204, 188 (100%), 160, 152, 138, 126, 110.81.

FTMS-MALDI: m/z: $(M+H)^+$ 314.1144

FT-IR: ($cm^1$) 2920, 2344, s, 1819 m, 1702 s, 1255, 1085 s, 1020 s, 797 s.

Molecular formula: $C_{15}H_{20}ClNO_4$

Example 2

Bioactivity Assays

Salinosporamide A shows strong activity against human colon cancer cells with an $IC_{50}$ of 0.011 µg/mL (see FIG. 4). The screening on antibacterial or antifungal activity shows no significant activity, see Table 1.

TABLE 1

| Assay | $IC_{50}$ of Salinosporamide A, (µg/mL) |
| --- | --- |
| HCT-116 | 0.011 |
| Candida albicans | 250 |
| Candida albicans (amphoterocin B resistant) | NSA* |
| Staphylococcus aureus (methecillin resistant) | NSA* |
| Enterococcus faecium (vanomycin resistant) | NSA* |

*NSA = no significant activity

Example 3

Determination of Absolute Stereochemistry

Figure 16:
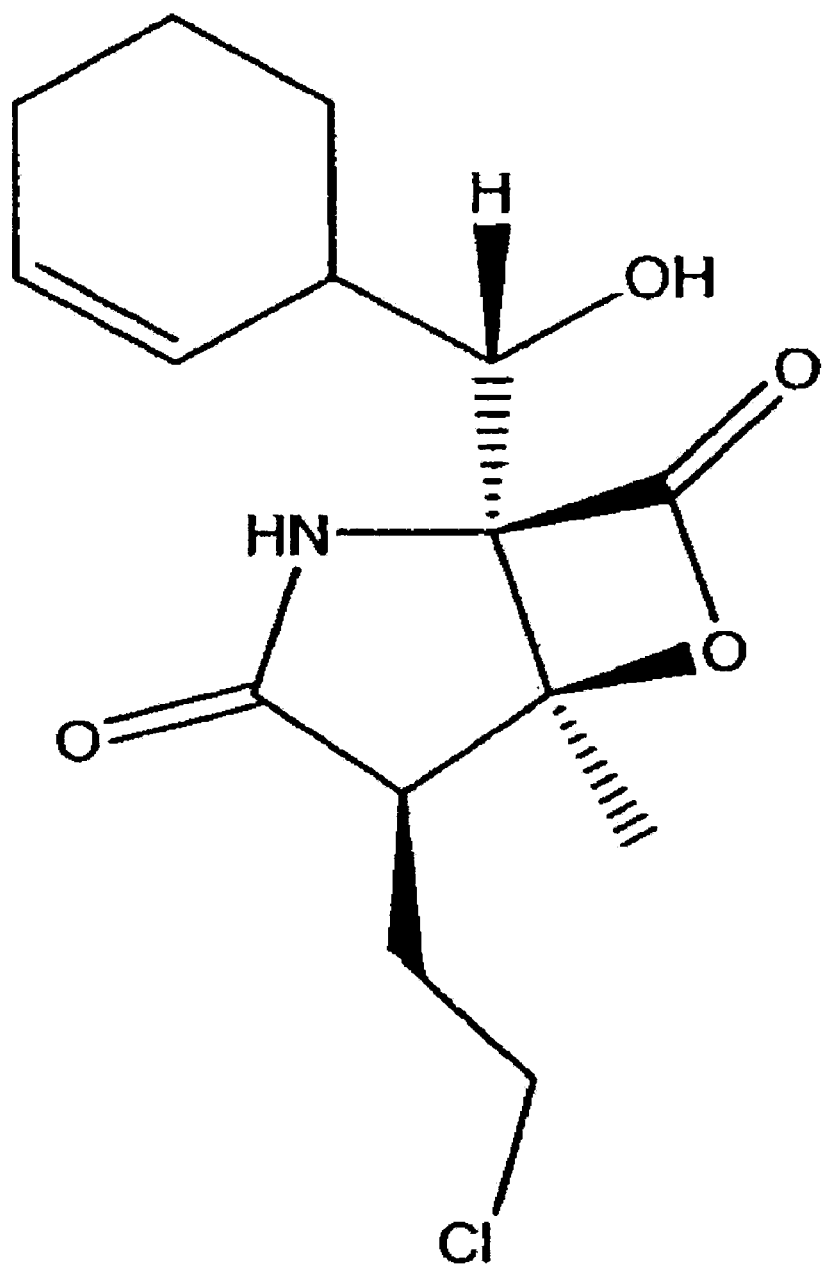
FIG. 16 depicts the chemical structure of an exemplary compound of the invention, salinosporamide A (structure V), with absolute stereochemistry.
Figure 17:
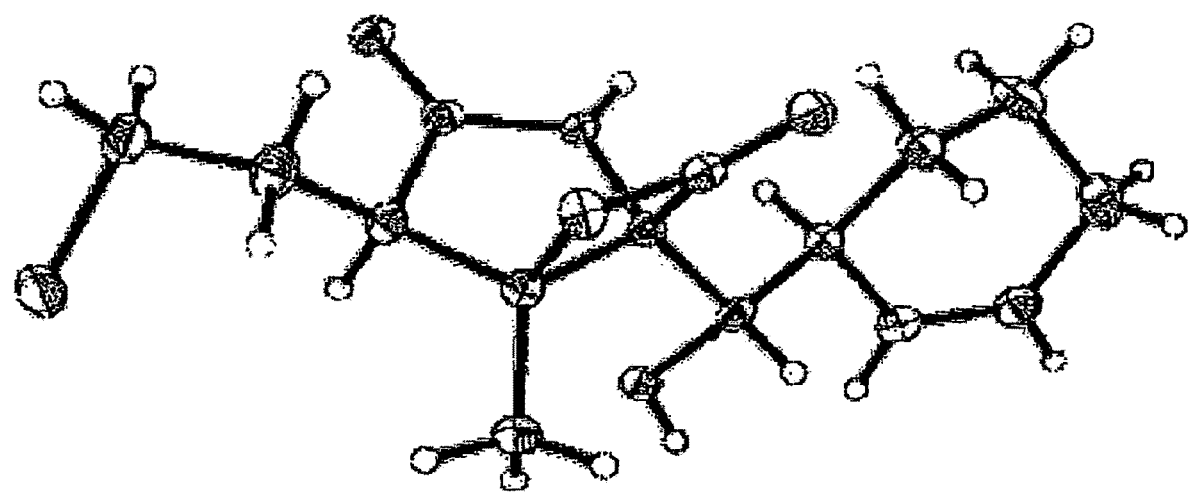
FIG. 17 ORTEP plot of the final X-ray structure of salinosporamide A, depicting the absolute stereochemistry.

Crystallization of a compound of structure I from ethyl acetate/iso-octane resulted in single, cubic crystals, which diffracted as a monoclinic system P2(1). The unusual high unit-cell volume of 3009 Å hosted four independent molecules in which different conformational positions were observed for the flexible chloroethyl substituent. The assignment of the absolute structure from the diffraction anisotropy of the chlorine substituent resolved the absolute stereochemistry of salinosporamide A as 2R,3S,4R,5S,6S (FIGS. 16 and 17) with a Flack parameter of 0.01 and an esd of 0.03.

Although the invention has been described with reference to the above examples, it will be understood that modifications and variations are encompassed within the spirit and scope of the invention. Accordingly, the invention is limited only by the following claims.

What is claimed is:

1. A method of treating a mammalian cell proliferative disorder comprising administering a pharmaceutical composition comprising a therapeutically effective amount of a compound of the structure (I):

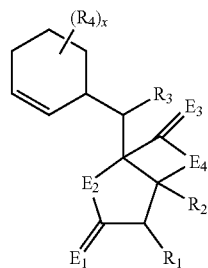

wherein:
R$_1$ to R$_3$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonamide or sulfuryl;
each R$_4$ is independently alkyl, substituted alkyl, alkenyl, substituted alkenyl, alkynyl, substituted alkynyl, aryl, substituted aryl, cycloalkyl, substituted cycloalkyl;
E$_1$ to E$_4$ are each independently —O, —NR$_5$, or —S, wherein R$_5$ is —H or C$_1$-C$_6$alkyl; and
X is 0 to 8.

2. The method of claim 1, wherein
R$_1$ is a substituted alkyl; R$_2$ is methyl; R$_3$ is hydroxyl;
each R$_4$ is independently alkyl, substituted alkyl, alkenyl, substituted alkenyl, alkynyl, substituted alkynyl, aryl, substituted aryl, cycloalkyl, substituted cycloalkyl;
E$_1$, E$_3$ and E$_4$ are —O,
E$_2$ is —NR$_5$, wherein R$_5$ is —H or C$_1$-C$_6$ alkyl; and
X is 0 to 8.

3. The method of claim 1, wherein the compound has the structure of formula (V):

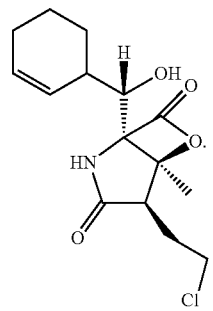

4. The method of claim 1, wherein the mammalian cell proliferative disorder is a neoplasm.
5. The method of claim 4, wherein the neoplasm is a cancer.
6. The method of claim 5, wherein the cancer is myeloma.
7. The method of claim 5, wherein the cancer is central nervous system (CNS) cancer.
8. The method of claim 5, wherein the cancer is Hodgkin's disease.
9. The method of claim 5, wherein the cancer is non-Hodgkin's disease.
10. The method of claim 5, wherein the cancer is renal cancer.
11. The method of claim 5, wherein the cancer is sarcoma cell of bone.
12. The method of claim 5, wherein the cancer is leukemia.

* * * * *